(12) United States Patent
Ni et al.

(10) Patent No.: US 10,563,219 B2
(45) Date of Patent: Feb. 18, 2020

(54) **CORN GENES *ZMSPL1* AND *ZMSPL2* AND USES THEREOF**

(71) Applicant: CHINA AGRICULTURAL UNIVERSITY, Beijing (CN)

(72) Inventors: Zhongfu Ni, Beijing (CN); Qixin Sun, Beijing (CN); Cheng Wang, Beijing (CN); Bo Wang, Beijing (CN); Yingyin Yao, Beijing (CN); Huiru Peng, Beijing (CN); Yirong Zhang, Beijing (CN); Zhaorong Hu, Beijing (CN)

(73) Assignee: China Agricultural University, Beijing (CN)

( * ) Notice: Subject to any disclaimer, the term of this patent is extended or adjusted under 35 U.S.C. 154(b) by 482 days.

(21) Appl. No.: 15/039,667

(22) PCT Filed: Nov. 29, 2013

(86) PCT No.: PCT/CN2013/001475
§ 371 (c)(1),
(2) Date: May 26, 2016

(87) PCT Pub. No.: WO2015/077904
PCT Pub. Date: Jun. 4, 2015

(65) Prior Publication Data
US 2017/0067071 A1    Mar. 9, 2017

(51) Int. Cl.
*C12N 15/29* (2006.01)
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS

| 2004/0019927 A1* | 1/2004 | Sherman | C07K 14/415 800/278 |
| 2009/0094717 A1* | 4/2009 | Troukhan | C07K 14/415 800/290 |
| 2012/0017338 A1* | 1/2012 | Wu | C07K 14/415 800/300 |

OTHER PUBLICATIONS

GenBank Accession NM_001362256 (2005). (Year: 2005).*
Wei et al. (Journal of experimental botany, vol. 69, No. 20 pp. 4675-4688 (2018)) (Year: 2018).*
Guo et al (2004, Proc. Natl. Acad. Sci. USA 101: 9205-9210). (Year: 2004).*
Salvi et al. (Proceedings of the National Academy of Sciences 104.27 (2007): 11376-11381). (Year: 2007).*
Fourgoux-Nicol et al. (Plant Mol. Biol. (1999) 40: 857-872). (Year: 1999).*
International Search Report & Written Opinion of the International Searching Authority dated Sep. 30, 2014 in PCT/CN2013/001475.

* cited by examiner

*Primary Examiner* — Charles Logsdon
(74) *Attorney, Agent, or Firm* — Womble Bond Dickinson (US) LLP; Kevin Fiala; Cristin Cowles

(57) ABSTRACT

The corn genes ZmSPL1 and ZmSPL2 are provided. The proteins encoded by these genes and the uses of these genes are also provided.

11 Claims, 18 Drawing Sheets

Specification includes a Sequence Listing.

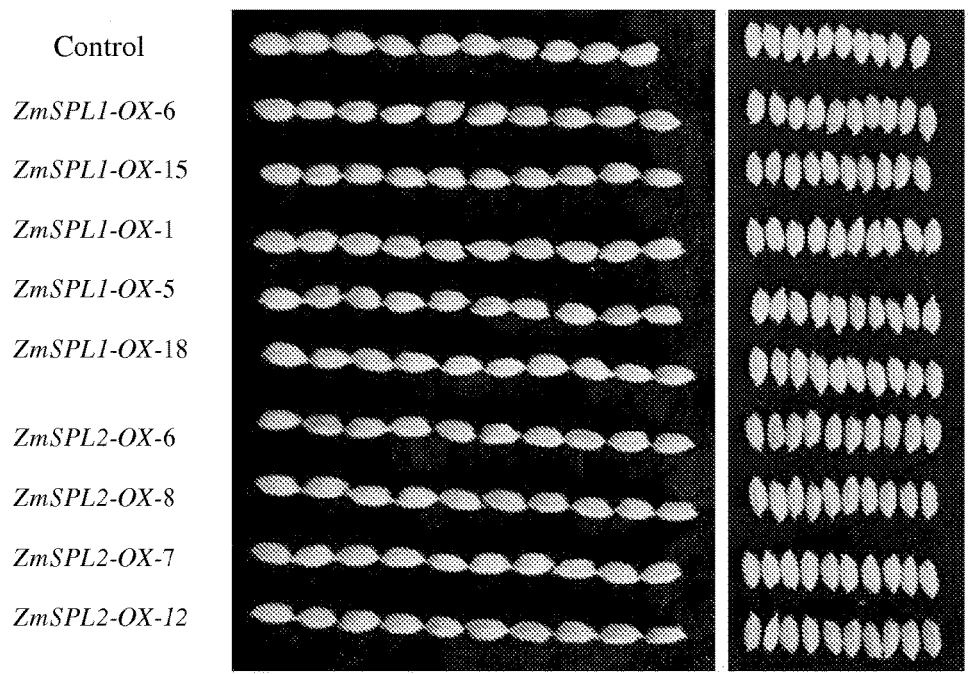
Figure 15. Comparison of grain phenotype between *ZmSPL1* and *ZmSPL2* overexpressed transgenic rice and control
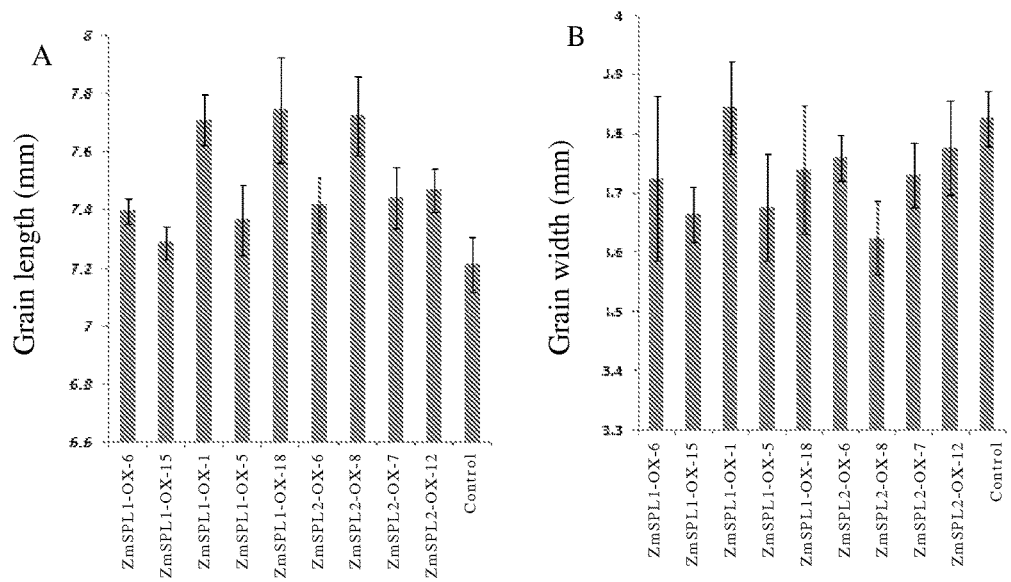
Figure 16. Comparison of grain length and width between *ZmSPL1* and *ZmSPL2* overexpressed transgenic rice and control

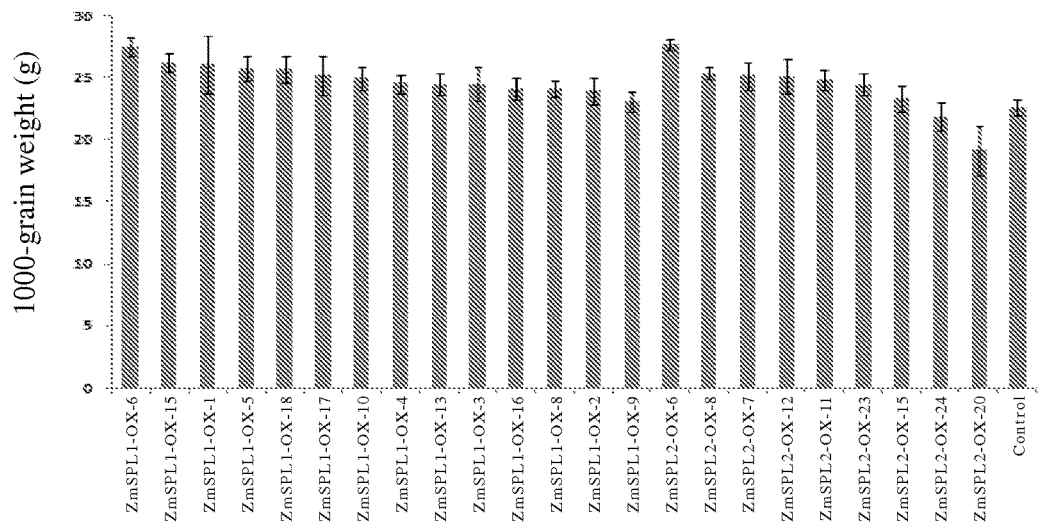

Figure 17. Comparison of 1000-grain weight between *ZmSPL1* and *ZmSPL2* overexpressed transgenic rice and control

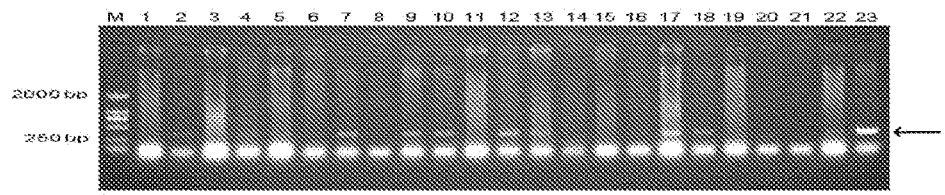

Figure 18. PCR identification of positive seedlings of *ZmSPL1* overexpressed transgenic corn
*M: marker having a molecular weight of 2000 bp; 1: water control; 2-22: different *ZmSPL1*-OX transgenic plant lines; 23: Positive plasmid

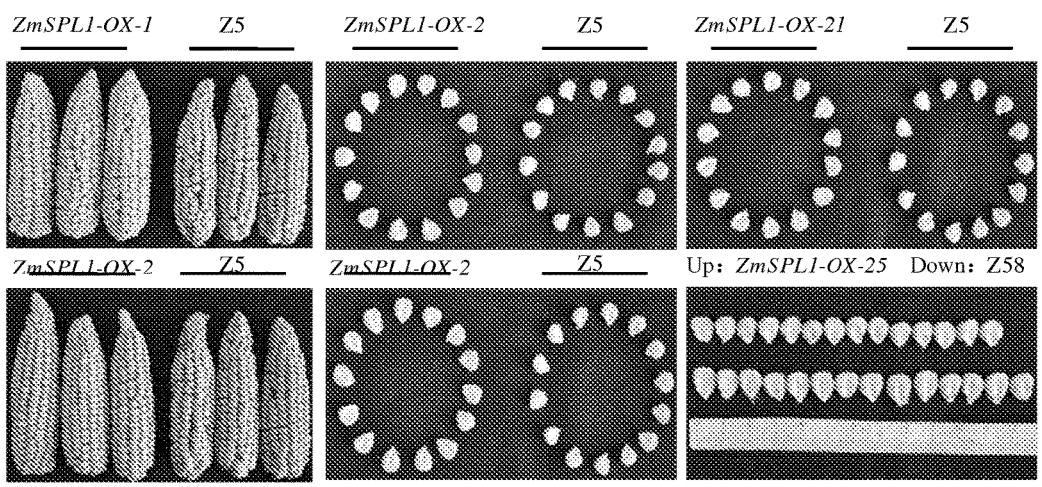

Figure 19. Comparison of spike characteristics between *ZmSPL1* overexpressed transgenic corn and Zhen58

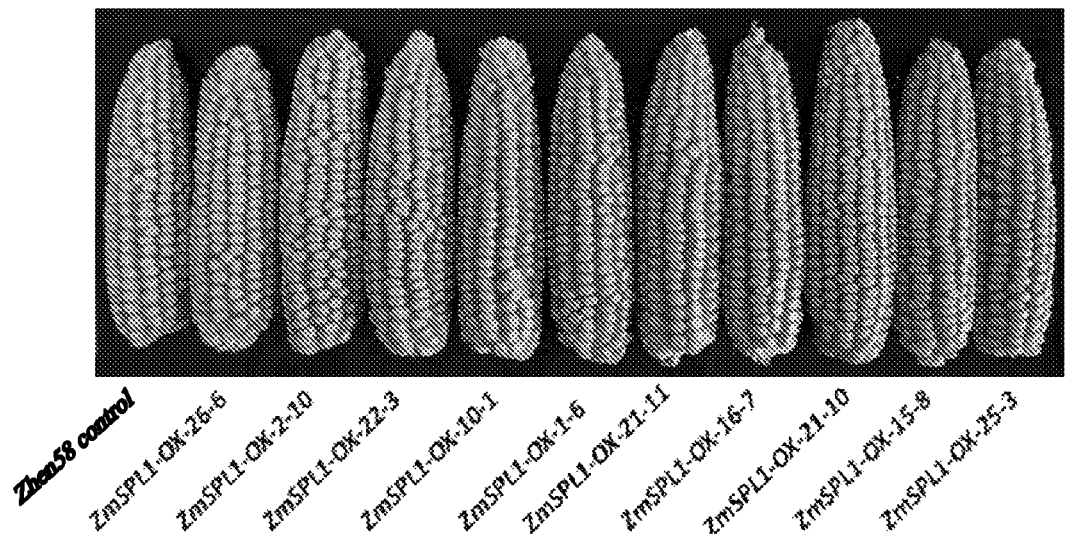
Figure 20. Comparison of spike length between *ZmSPL1* overexpressed line and Zhen58 control
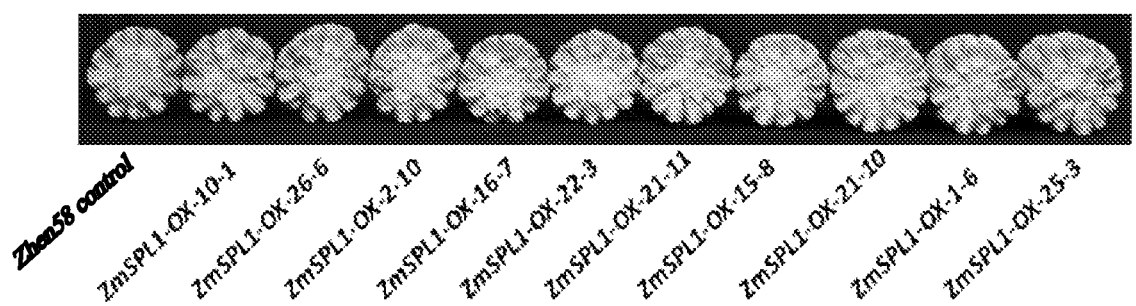
Figure 21. Comparison of spike width between *ZmSPL1* overexpressed line and Zhen58 control

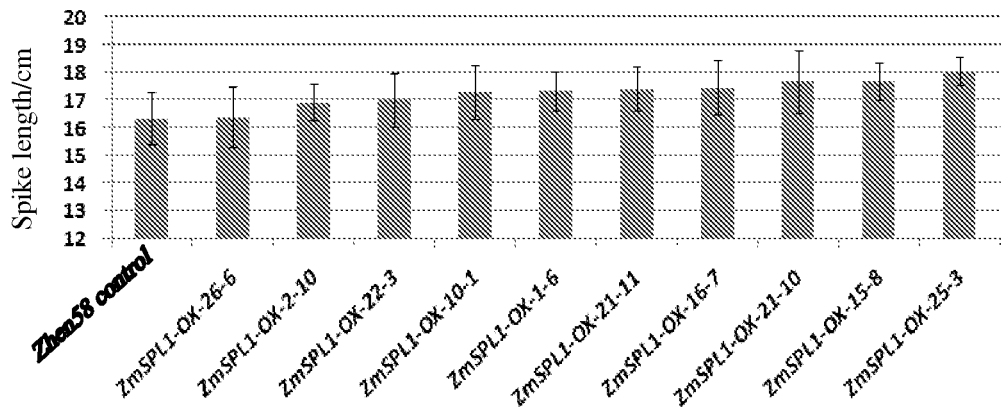
Figure 22. Comparison of spike length between *ZmSPL1* overexpressed line and Zhen58 control
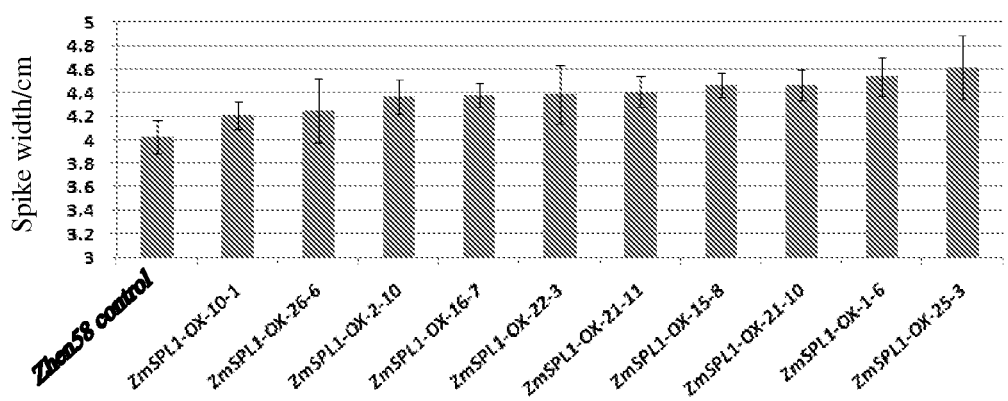
Figure 23. Comparison of spike width between *ZmSPL1* overexpressed line and Zhen58 control

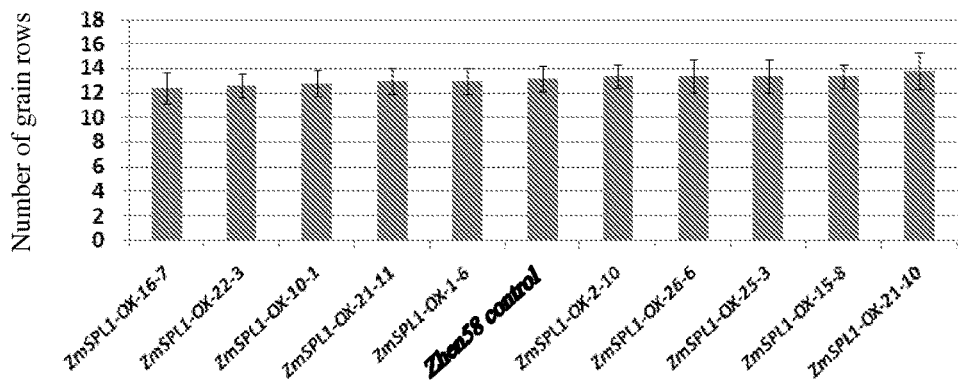
Figure 24. Comparison of number of grain rows in a spike between *ZmSPL1* overexpressed line and Zhen58 control
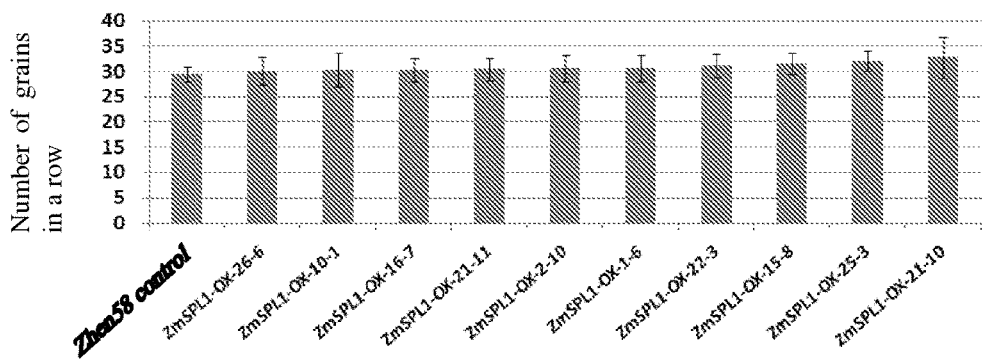
Figure 25. Comparison of number of grains in a row between *ZmSPL1* overexpressed line and Zhen58 control

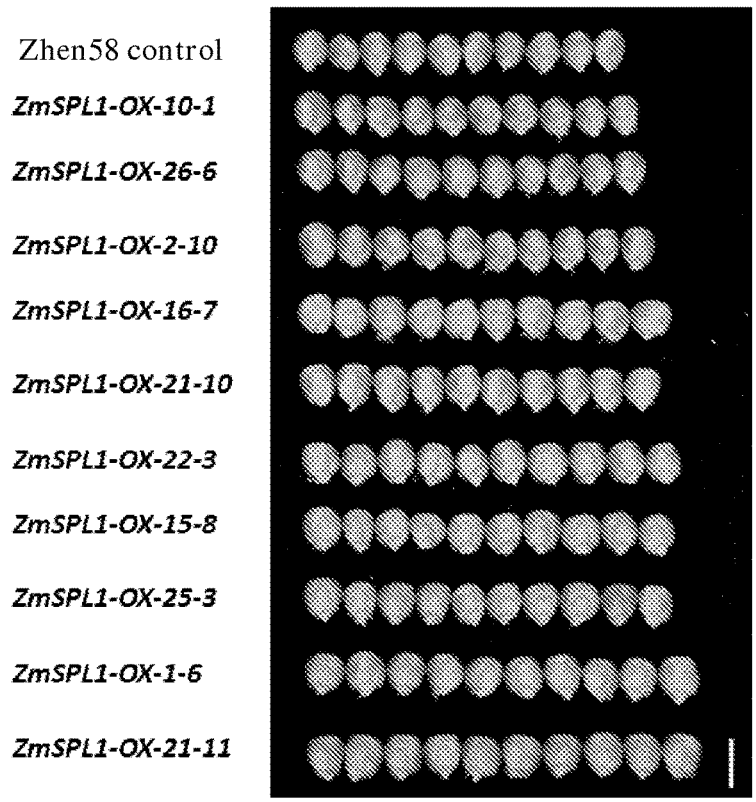
Figure 26. Comparison of grain size between *ZmSPL1* overexpressed line and Zhen58 control
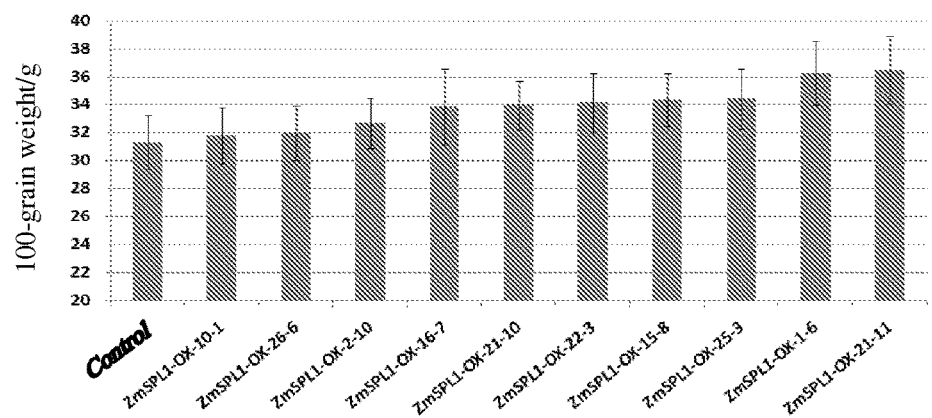
Figure 27. Comparison of 100-grain weight between *ZmSPL1* overexpressed line and Zhen58 control

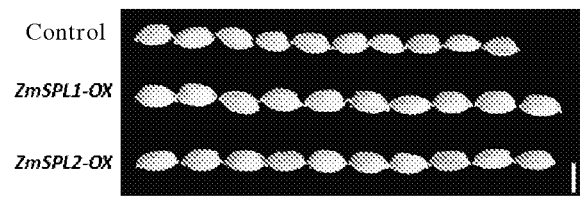
Figure 28. Comparison of grain length between *ZmSPL-OX* rice and control
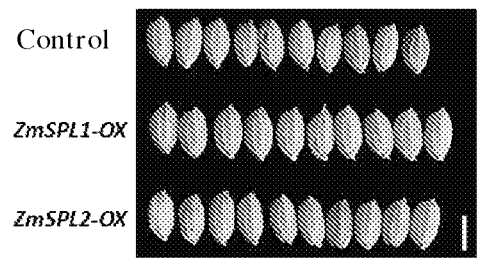
Figure 29. Comparison of grain width between *ZmSPL-OX* rice and control
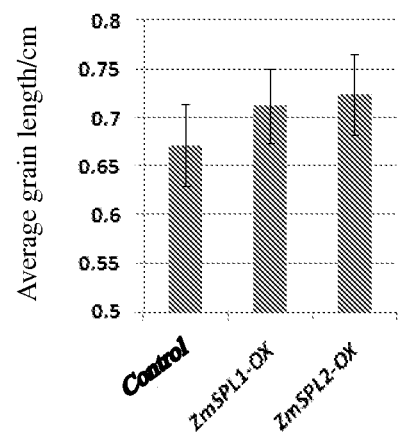
Figure 30. Comparison of average grain length

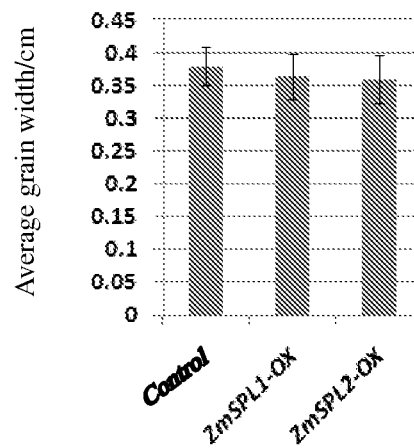
Figure 31. Comparison of average grain width
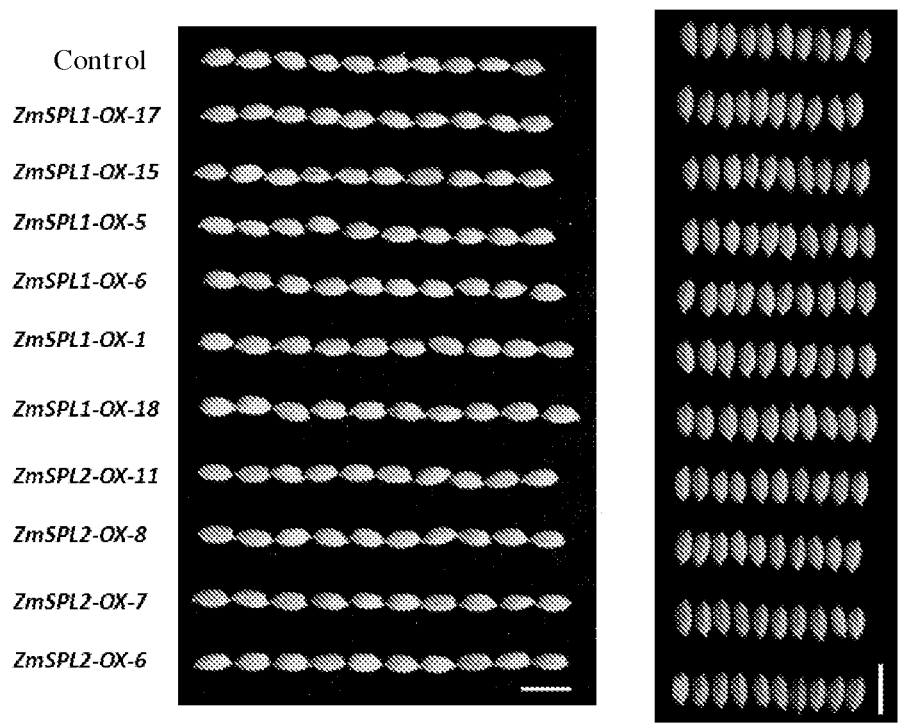
Figure 32. Comparison of grain phenotype between *ZmSPL1* and *ZmSPL2* transgenic rice and control

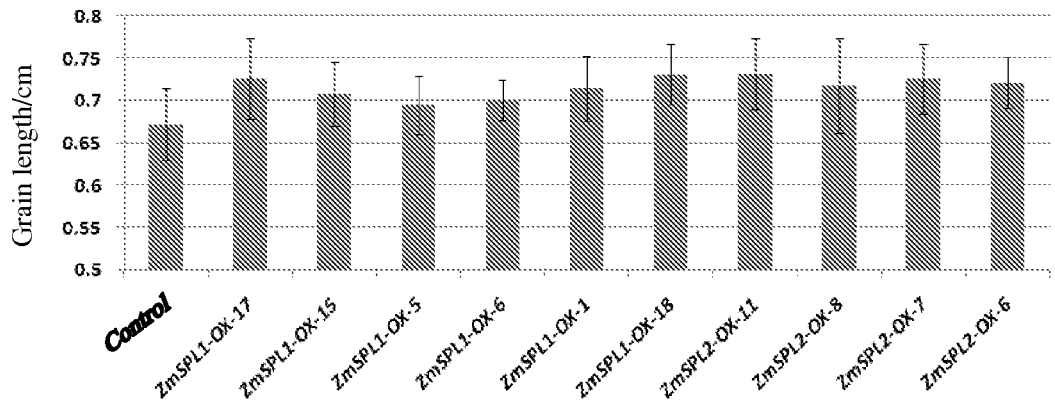
Figure 33. Comparison of grain length between *ZmSPL1* and *ZmSPL2* transgenic rice and control
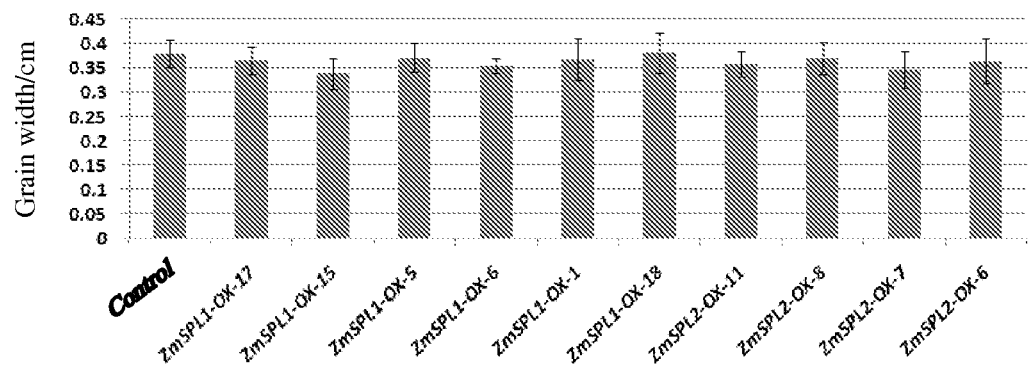
Figure 34. Comparison of grain width between *ZmSPL1* and *ZmSPL2* transgenic rice and control
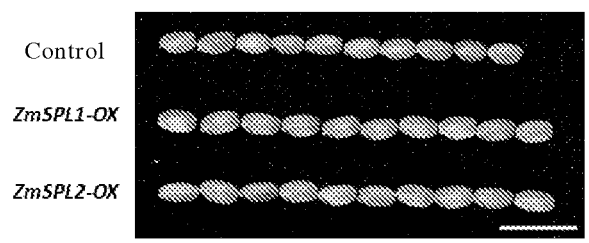
Figure 35. Comparison of grain length between *ZmSPL-OX* rice and control

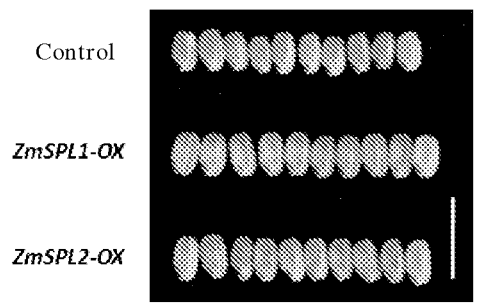
Figure 36. Comparison of grain width between *ZmSPL-OX* rice and control
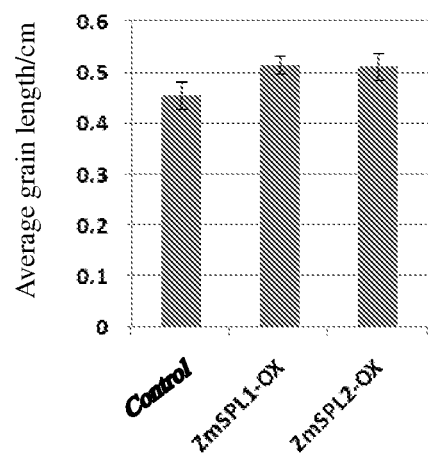
Figure 37. Comparison of average grain length
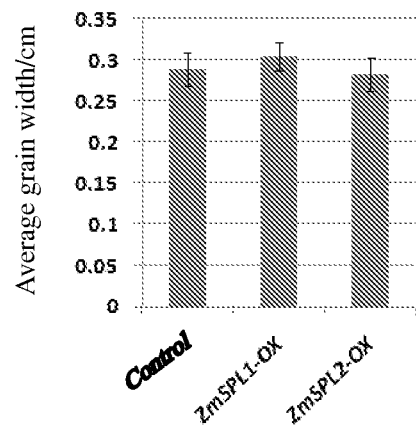
Figure 38. Comparison of average grain width

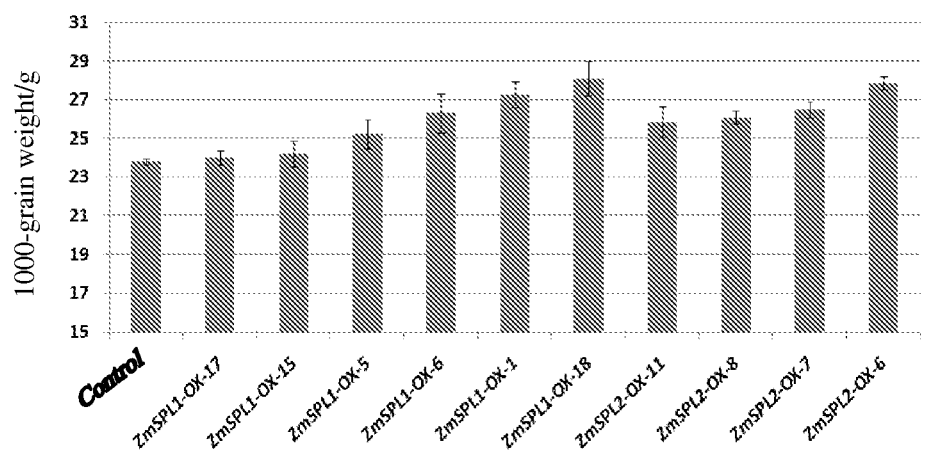
Figure 39. Comparison of 1000-grain weight between *ZmSPL1* and *ZmSPL2* overexpressed transgenic rice and control

SEQUENCE LISTING

<160> NUMBER OF SEQ ID NOS: 13

<210> SEQ ID NO 1
<211> LENGTH: 2919
<212> TYPE: DNA
<213> ORGANISM: Zea mays

<400> SEQUENCE: 1

```
atggaggccg ccaggttcgg cgcgcggagc agccacttgt acggcagcgg gctgggcgag      60
cttgacctca caggcgcga gagcagggtg tttggctggg atctcaacga gtggagctgg     120
gacagtcagc gctttactgc cacgccggtg cctgtcgagg cggcgaatgg ctctggactg     180
aacagctcgc cgtcatcgtc cgaggaagcc ggggaagaga tggctaagaa tggtggcttg     240
ggaggtgaaa ctgacaagag gaaaagggcc gtggtcattg atgacgatga tgatgatgaa     300
acggaggatc aggacacggt cgtgaatggt ggcgggtcac tcagcctgat aataggggt      360 agtgctgctg gtgctggagc gatggagaac ggcgatgtaa atgaggatga gagaaatgga     420
aagaaggtca gggtgcaagg aggcggctca agtgggccgg catgccaggt tgagggctgc     480
ggagcagatc tgactgcagc aaaggattat caccgtcgac acaaggtctg cgggatgcat     540
gctaaggcca ccaccgccgt ggtcggaaac actgtccaga ggttctgcca gcaatgcagt     600
agatttcacc ttcttcaaga atttgatgaa gggaagcgaa gttgccgtcg acgcttagca     660
ggccacaata aacggaggag gaaaacccgc cctgatactg caagttgtgg gactgcttca     720
attgaggaca aaatcagcaa ttatctgctg ttgagcctta ttggaatctg tgctaatttg     780
aactctgata tgttcagca ttcaaatggc caggagttgc tatccactct tttgaagaac     840
ctagggtctg ttgccaaatc actggagcca aaagaactat gtaaactcct ggaggcatac     900
caaagcctgc aaaatggatc aaatgctgga acctctggaa cagctaatgc cacagaagag     960
gctgcagggc catctaactc taagttgcct ttcgtgaatg gcagtcattg tggacatgca    1020
tcatcatctg ttgtgccagt acagtcgaag gctaccatag tggtaactcc agagcccgca    1080
tcatgcaagc ttaaggattt tgatctgaat gacacttgca atgatatgga aggctttgag    1140
gatggacaag aaggttcacc tacacctgcc tttaagacag ctgactctcc taattgtgca    1200
tcatggatgc aacaagattc tactcaaagt ccaccgcaga ctagtggcaa ctcagattca    1260
acatcaacac aatcattgtc aagctcaaat ggagacgctc agtgccgaac tgataagatt    1320
gtcttcaagc tttttgacaa agttcccagt gatttacccc cagttttgcg gtcacagatt    1380
cttggttggt tgtcaagtag ccctactgat atagagagcc atattagacc tgggtgtatt    1440
attctaacaa tatatctacg gttagttgag tctgcatggc aagagctttc tgagaatatg    1500
agcctgcacc tggataagct tttgagtagc tccactgaca gcttttgggc atctggcttg    1560
```

-continued

```
gtatttgtga tggttcggcg tcgcttagct tttatgctca atggtcaaat tatgttggac    1620 agaccctgg cacccagttc tcatcattac tgcaagattt tatgtgtcaa acctgttgct    1680
gcaccttatt ctgcaacaat aagtttcaga gtcgaaggat ctaatctact cagtacttcc    1740
ccaaggctaa tttgttcatt tgaaggacgt tgtatattcc aggaagacac agactctgta    1800
gcagaaaatg atgagtatga ggatagggcc atcgaatgcc tcagtttttg ttgttccgtt    1860
cctggtccaa aggaagagg atttatagag gttgaagata gtggttttag caatggcttc    1920
ttccccttca taattgctga gaaagacata tgctttgagg tttctgagct ggagagcata    1980
tttgagtcct ccagtatcga acatgcagat gctaatgata atgccaggga acaagctctg    2040
gagtttctaa atgagctggg ttggcttctt cacagagcga acagaatgtc taaagagaat    2100
gtaactgata catctgtagc taccttagc atgtggggat tcaggaatct tggtgtattt    2160
gccatggagc gggagtggtg tgctgtgatc aaaatgctgt tagatttctt atttattggc    2220
cttgtcgatg tggggtcccg atctccagaa ggggtggtgc tttcagaaaa tttgttgcat    2280
gctgctgtgc ggaggaagtc tgttaacatg gctagatttc tgctgagata cagaccaaac    2340
aaaaactcca aggggactgc acagacatac ttatttagac ctgatgctct gggcccgtca    2400
atgattaccc ccctccctat agcagctgcc actagtgatg cagaggatga gttggatgtg    2460
ctgaccgatg atcctggact gattggaatt agtgcttgga gcaatgcacg ggacggaaca    2520
ggttttaccc cagaagacta tgctcggcag agaggcaatg atgcttacct gaatctggtc    2580
caaaagaaga ttgataagca tcttggcaaa ggccgtgttg tcctcggtgt tccgagcagt    2640
atatgctctg taataactga tggtgttaag cctggcgatg ttagcctcga gatctgcatg    2700
ccaatgtctg catcagtgcc aggttgcctc ctctacagcc gtcaggcacg ggtgtatccg    2760
aactctacat cgaggacctt cctttacagg ccagcaatgt tgactgtgat gggagttgct    2820
gtggtctgtg tctgcgtggg catactcctc cacacctttc cgagggttta tgccgcgccc    2880
acattcagat gggagttgct ggagcgtgga cccatgtaa                          2919
```

<210> SEQ ID NO 2
<211> LENGTH: 972
<212> TYPE: PRT
<213> ORGANISM: Zea mays

<400> SEQUENCE: 2

```
Met Glu Ala Ala Arg Phe Gly Ala Arg Ser Ser His Leu Tyr Gly Ser
1               5                   10                  15

Gly Leu Gly Glu Leu Asp Leu Asn Arg Arg Glu Ser Arg Val Phe Gly
            20                  25                  30

Trp Asp Leu Asn Glu Trp Ser Trp Asp Ser Gln Arg Phe Thr Ala Thr
        35                  40                  45

Pro Val Pro Val Glu Ala Ala Asn Gly Ser Gly Leu Asn Ser Ser Pro
    50                  55                  60

Ser Ser Ser Glu Glu Ala Gly Glu Glu Met Ala Lys Asn Gly Gly Leu
65                  70                  75                  80

Gly Gly Glu Thr Asp Lys Arg Lys Arg Ala Val Val Ile Asp Asp
            85                  90                  95

Asp Asp Asp Glu Thr Glu Asp Gln Asp Thr Val Val Asn Gly Gly Gly
            100                 105                 110

Ser Leu Ser Leu Ile Ile Gly Gly Ser Ala Ala Gly Ala Gly Ala Met
        115                 120                 125
```

```
Glu Asn Gly Asp Val Asn Asp Glu Arg Asn Gly Lys Lys Val Arg
130                 135                 140

Val Gln Gly Gly Gly Ser Ser Gly Pro Ala Cys Gln Val Glu Gly Cys
145                 150                 155                 160

Gly Ala Asp Leu Thr Ala Ala Lys Asp Tyr His Arg Arg His Lys Val
                165                 170                 175

Cys Gly Met His Ala Lys Ala Thr Thr Ala Val Val Gly Asn Thr Val
            180                 185                 190

Gln Arg Phe Cys Gln Gln Cys Ser Arg Phe His Leu Leu Gln Glu Phe
        195                 200                 205

Asp Glu Gly Lys Arg Ser Cys Arg Arg Leu Ala Gly His Asn Lys
    210                 215                 220

Arg Arg Arg Lys Thr Arg Pro Asp Thr Ala Ser Cys Gly Thr Ala Ser
225                 230                 235                 240

Ile Glu Asp Lys Ile Ser Asn Tyr Leu Leu Leu Ser Leu Ile Gly Ile
                245                 250                 255

Cys Ala Asn Leu Asn Ser Asp Asn Val Gln His Ser Asn Gly Gln Glu
            260                 265                 270

Leu Leu Ser Thr Leu Leu Lys Asn Leu Gly Ser Val Ala Lys Ser Leu
        275                 280                 285

Glu Pro Lys Glu Leu Cys Lys Leu Leu Glu Ala Tyr Gln Ser Leu Gln
    290                 295                 300

Asn Gly Ser Asn Ala Gly Thr Ser Gly Thr Ala Asn Ala Thr Glu Glu
305                 310                 315                 320

Ala Ala Gly Pro Ser Asn Ser Lys Leu Pro Phe Val Asn Gly Ser His
                325                 330                 335

Cys Gly His Ala Ser Ser Ser Val Val Pro Val Gln Ser Lys Ala Thr
            340                 345                 350

Ile Val Val Thr Pro Glu Pro Ala Ser Cys Lys Leu Lys Asp Phe Asp
        355                 360                 365

Leu Asn Asp Thr Cys Asn Asp Met Glu Gly Phe Glu Asp Gly Gln Glu
    370                 375                 380

Gly Ser Pro Thr Pro Ala Phe Lys Thr Ala Asp Ser Pro Asn Cys Ala
385                 390                 395                 400

Ser Trp Met Gln Gln Asp Ser Thr Gln Ser Pro Pro Gln Thr Ser Gly
                405                 410                 415

Asn Ser Asp Ser Thr Ser Thr Gln Ser Leu Ser Ser Asn Gly Asp
            420                 425                 430

Ala Gln Cys Arg Thr Asp Lys Ile Val Phe Lys Leu Phe Asp Lys Val
        435                 440                 445

Pro Ser Asp Leu Pro Pro Val Leu Arg Ser Gln Ile Leu Gly Trp Leu
    450                 455                 460

Ser Ser Ser Pro Thr Asp Ile Glu Ser His Ile Arg Pro Gly Cys Ile
465                 470                 475                 480

Ile Leu Thr Ile Tyr Leu Arg Leu Val Glu Ser Ala Trp Gln Glu Leu
                485                 490                 495

Ser Glu Asn Met Ser Leu His Leu Asp Lys Leu Leu Ser Ser Ser Thr
            500                 505                 510

Asp Ser Phe Trp Ala Ser Gly Leu Val Phe Val Met Val Arg Arg Arg
        515                 520                 525

Leu Ala Phe Met Leu Asn Gly Gln Ile Met Leu Asp Arg Pro Leu Ala
    530                 535                 540

Pro Ser Ser His His Tyr Cys Lys Ile Leu Cys Val Lys Pro Val Ala
```

```
            545                 550                 555                 560

Ala Pro Tyr Ser Ala Thr Ile Ser Phe Arg Val Glu Gly Ser Asn Leu
                565                 570                 575

Leu Ser Thr Ser Pro Arg Leu Ile Cys Ser Phe Glu Gly Arg Cys Ile
                580                 585                 590

Phe Gln Glu Asp Thr Asp Ser Val Ala Glu Asn Asp Glu Tyr Glu Asp
                595                 600                 605

Arg Ala Ile Glu Cys Leu Ser Phe Cys Cys Ser Val Pro Gly Pro Arg
610                 615                 620

Gly Arg Gly Phe Ile Glu Val Glu Asp Ser Gly Phe Ser Asn Gly Phe
625                 630                 635                 640

Phe Pro Phe Ile Ile Ala Glu Lys Asp Ile Cys Phe Glu Val Ser Glu
                645                 650                 655

Leu Glu Ser Ile Phe Glu Ser Ser Ile Glu His Ala Asp Ala Asn
                660                 665                 670

Asp Asn Ala Arg Glu Gln Ala Leu Glu Phe Leu Asn Glu Leu Gly Trp
                675                 680                 685

Leu Leu His Arg Ala Asn Arg Met Ser Lys Glu Asn Val Thr Asp Thr
            690                 695                 700

Ser Val Ala Thr Phe Ser Met Trp Gly Phe Arg Asn Leu Gly Val Phe
705                 710                 715                 720

Ala Met Glu Arg Glu Trp Cys Ala Val Ile Lys Met Leu Leu Asp Phe
                725                 730                 735

Leu Phe Ile Gly Leu Val Asp Val Gly Ser Arg Ser Pro Glu Gly Val
                740                 745                 750

Val Leu Ser Glu Asn Leu Leu His Ala Ala Val Arg Arg Lys Ser Val
            755                 760                 765

Asn Met Ala Arg Phe Leu Leu Arg Tyr Arg Pro Asn Lys Asn Ser Lys
            770                 775                 780

Gly Thr Ala Gln Thr Tyr Leu Phe Arg Pro Asp Ala Leu Gly Pro Ser
785                 790                 795                 800

Met Ile Thr Pro Leu Pro Ile Ala Ala Ala Thr Ser Asp Ala Glu Asp
                805                 810                 815

Glu Leu Asp Val Leu Thr Asp Pro Gly Leu Ile Gly Ile Ser Ala
                820                 825                 830

Trp Ser Asn Ala Arg Asp Gly Thr Gly Phe Thr Pro Glu Asp Tyr Ala
                835                 840                 845

Arg Gln Arg Gly Asn Asp Ala Tyr Leu Asn Leu Val Gln Lys Lys Ile
850                 855                 860

Asp Lys His Leu Gly Lys Gly Arg Val Val Leu Gly Val Pro Ser Ser
865                 870                 875                 880

Ile Cys Ser Val Ile Thr Asp Gly Val Lys Pro Gly Asp Val Ser Leu
                885                 890                 895

Glu Ile Cys Met Pro Met Ser Ala Ser Val Pro Gly Cys Leu Leu Tyr
                900                 905                 910

Ser Arg Gln Ala Arg Val Tyr Pro Asn Ser Thr Ser Arg Thr Phe Leu
            915                 920                 925

Tyr Arg Pro Ala Met Leu Thr Val Met Gly Val Ala Val Val Cys Val
            930                 935                 940

Cys Val Gly Ile Leu Leu His Thr Phe Pro Arg Val Tyr Ala Ala Pro
945                 950                 955                 960

Thr Phe Arg Trp Glu Leu Leu Glu Arg Gly Pro Met
                965                 970
```

<210> SEQ ID NO 3
<211> LENGTH: 3339
<212> TYPE: DNA
<213> ORGANISM: Zea mays

<400> SEQUENCE: 3

| | | | | | | |
|---|---|---|---|---|---|---|
| atgcagaggg | aggtgggccc | gcaggtggcc | cctccgctct | tcatccacca | ccagatccag | 60 |
| ccgatgcctc | cccacgccgc | ggccgccgtg | aagaagcgcg | ccagccgtg | tccggccgcc | 120 |
| gcggcggcgc | ccgcggaggc | cgctgcgggg | aactggaacc | ccaggctgtg | ggactgggac | 180 |
| agccgcgcgc | tcaccgccag | gccgtcggcc | gatgcactcc | gcctcgccgg | tggccagccc | 240 |
| cagccccagc | cccagcaggc | ggccgaggtg | caccgtcagg | gggccggagg | aagcggcgcg | 300 |
| ctgaagctcc | agctcggccc | gcgggaaggc | tccacggccc | cgacggacgc | cagcccgacg | 360 |
| gctcccgcgg | cgtcgctgtc | gccgtccccg | cctgcttcgg | ggcaggacct | ggtggtcagg | 420 |
| ccgagcaagc | gggtgcggtc | aggatcgcca | ggcagcgcgg | gcgtggcgg | tggcggggct | 480 |
| gccaacggag | gcgcgggcta | cccgatgtgc | caggtggatg | agtgccgagc | ggatctgacc | 540 |
| ggcgccaagg | actaccacag | gaggcacaag | gtctgcgaga | cccacagcaa | gaccatcagg | 600 |
| gccgtcgtcg | ccaaccaggc | gcagcgcttc | tgccagcagt | gtagtagatt | tcacccactc | 660 |
| gcggagtttg | acgagggtaa | gaggagctgc | ggcgtaggc | ttgctgggca | caaccggcgg | 720 |
| agaagaaaaa | cccagccagc | agatgtttct | tcgcagttgc | tgctacctgg | aaaccaagaa | 780 |
| aatgcagcaa | ataggacgca | ggatattgtc | aatctaatta | cagtgattgc | gcacttgcat | 840 |
| ggttctagcg | tcggtaaagt | gcctagcatt | cctcccatac | cagataagca | gaatctggtt | 900 |
| gaaattatca | gcaaaataaa | ttcattcaac | aatatgaccct | ctgcggacaa | atctcctcca | 960 |
| tctgaagtcg | ttgatttgga | tgctttgcaa | gagcaacaag | tgcaacggca | ggattctgtg | 1020 |
| gggaagacga | ccaacggaat | cgacaagcaa | actgtgccat | caaccatgga | tttgctagga | 1080 |
| gttttttccaa | ctggccttgc | aacttcaaca | cctgagacca | atacatctca | gtcccaaggg | 1140 |
| agcagtgaca | gcagtggtaa | taacaagagc | aagagccatt | caacagagcc | agtaactgtt | 1200 |
| gtaaattcac | atgataaatc | aacccgagat | ttctctgctg | ctggtttcat | gagaagcaac | 1260 |
| agcacacacg | aaagccaacc | tcatatatac | aagcagacag | aacaagaaac | cagaccatac | 1320 |
| ttgtcactgc | agctgtttgg | cagcactgag | gaggattttc | cacctaagat | ggactcagtg | 1380 |
| aataagtact | tatcttctga | gagtagcaat | cctctggatg | agagatctcc | ttcatcctct | 1440 |
| ccgcctataa | cccgcaagtt | tttccccata | cactcggttg | atgaagaggt | tcggcaccct | 1500 |
| catattacag | attatgggga | agatgctacg | atgggtgaag | ttagcacaaa | tcaggcatgg | 1560 |
| ttggcaccac | cacttgatct | cttcaaggat | tcagagcgtc | ccatcgagaa | cggatcgcca | 1620 |
| ccaaatcctg | gttaccagtc | ctgctatgcc | tcaacatctt | gttcagatca | ttcaccttca | 1680 |
| acctcaaact | cagatggaca | ggatcggact | ggtaggatta | ttttaagct | gtttggcaag | 1740 |
| gaacctagca | caatacctgg | gaaccttcgt | gatgatatag | taaattggct | caaacacagc | 1800 |
| cctactgaaa | tggagggtta | cattcgcccc | ggttgccttg | tactatccat | gtacctatta | 1860 |
| atgccgggta | ttgcatggga | tgagcttgaa | gaaaatctcc | tccagagagt | aaactcatta | 1920 |
| gttcaaagtt | ctgatttgga | tttctggaga | aaaggaaggt | ttttagttcg | aaccaactcc | 1980 |
| cagttggtat | catataaagc | aggaatgacc | cgtttatcga | aatcgtggag | aacatggaat | 2040 |
| accccctgaat | tgaccccttgt | gtcaccaatt | gctgttgttg | gtgggcagaa | gacctccctc | 2100 |

```
attcttaaag gccgcaatct atctattcct ggcacacaga tccactgtac aagcataggg    2160
aagtacatat ccaaagaagt tctgtgctca gcatatccag gtaccatata tgatgattca    2220
ggtgttgaga catttgactt gccaggacaa ccagatctta ttcttgggcg ctgctttgtt    2280
gaggtagaaa acaggttcag gggtaacagc ttccctgtta ttgttgctag ttcaagcgtt    2340
tgccaggagt tgcgaaatct agaagttgag ttcgaggatt cgcaggttct tgatgtttct    2400
tcggatggtc agattcatga ttctcggcag ccaaagacat cggttcaagt tctgcacttc    2460
cttaatgaac tcggctggct ctttcagagg gcttctgcct gtacatcgtc caccagatct    2520
gatgtgtctg atttggattt gattcggttt tcaaccgcac ggttcagata ccttttactg    2580
ttctgtagtg agcgcgactg gtgctctctt actaaaacac ttctggacat tcttgccaag    2640
agaagcctgg ccagcgagga actatcaaag gagactatgg agatgctggc tgagattcac    2700
ctcctgaaca gagcagtaaa aagaaagagt aggaacatgg tgcacctact tgtgaagttc    2760
gttgtaattt gccccgacaa ttccaaggtt taccccttcc ttccgaactt gcctggccct    2820
ggtggtttaa ctccgctgca tcttgctgcg tccatcgaga atgcagagga tatagttgac    2880
gccttgacag acgaccctca acagactggt gtaacctgtt ggcagacagt tctagacgac    2940
gacggccaat ctcccgaaac atatgccaag ttgaggaacc ataattccta taatgagctc    3000
gtagcgcaaa agctggtgga catgaagaac aaccaggtca cagtaagggt taacggcgat    3060
gggattcgtg cggatcggtt aggaaatgat gttggtgacc gcaaaagatc tggggttcag    3120
gcgctgcaaa taagatcctg ctcccagtgt gccattctgg agtctggtgt gctaatgcag    3180
cccgtgcggt caaggggggtt ccttgctcgg ccctatatcc attcgatgct tgctatagcg    3240
gcagtatgcg tctgcgtctg tgtattcatg cgagcgttgc tgcggatcaa ttctggtaaa    3300
tccttcaagt gggagaggct ggattatggt acgatataa                           3339

<210> SEQ ID NO 4
<211> LENGTH: 1112
<212> TYPE: PRT
<213> ORGANISM: Zea mays

<400> SEQUENCE: 4

Met Gln Arg Glu Val Gly Pro Gln Val Ala Pro Pro Leu Phe Ile His
1               5                   10                  15

His Gln Ile Gln Pro Met Pro Pro His Ala Ala Ala Ala Val Lys Lys
            20                  25                  30

Arg Gly Gln Pro Cys Pro Ala Ala Ala Ala Pro Ala Glu Ala Ala
        35                  40                  45

Ala Gly Asn Trp Asn Pro Arg Leu Trp Asp Trp Asp Ser Arg Ala Leu
    50                  55                  60

Thr Ala Arg Pro Ser Ala Asp Ala Leu Arg Leu Ala Gly Gly Gln Pro
65                  70                  75                  80

Gln Pro Gln Pro Gln Gln Ala Ala Glu Val His Arg Gln Gly Ala Gly
                85                  90                  95

Gly Ser Gly Ala Leu Lys Leu Gln Leu Gly Pro Arg Glu Gly Ser Thr
            100                 105                 110

Ala Pro Thr Asp Ala Ser Pro Thr Ala Pro Ala Ala Ser Leu Ser Pro
        115                 120                 125

Ser Pro Pro Ala Ser Gly Gln Asp Leu Val Val Arg Pro Ser Lys Arg
    130                 135                 140

Val Arg Ser Gly Ser Pro Gly Ser Ala Gly Gly Gly Gly Gly Gly Ala
145                 150                 155                 160
```

```
Ala Asn Gly Gly Ala Gly Tyr Pro Met Cys Gln Val Asp Glu Cys Arg
                165                 170                 175

Ala Asp Leu Thr Gly Ala Lys Asp Tyr His Arg His Lys Val Cys
            180                 185                 190

Glu Thr His Ser Lys Thr Ile Arg Ala Val Val Ala Asn Gln Ala Gln
            195                 200                 205

Arg Phe Cys Gln Gln Cys Ser Arg Phe His Pro Leu Ala Glu Phe Asp
        210                 215                 220

Glu Gly Lys Arg Ser Cys Arg Arg Leu Ala Gly His Asn Arg Arg
225                 230                 235                 240

Arg Arg Lys Thr Gln Pro Ala Asp Val Ser Ser Gln Leu Leu Leu Pro
            245                 250                 255

Gly Asn Gln Glu Asn Ala Ala Asn Arg Thr Gln Asp Ile Val Asn Leu
            260                 265                 270

Ile Thr Val Ile Ala His Leu His Gly Ser Ser Val Gly Lys Val Pro
        275                 280                 285

Ser Ile Pro Pro Ile Pro Asp Lys Gln Asn Leu Val Glu Ile Ile Ser
        290                 295                 300

Lys Ile Asn Ser Phe Asn Asn Met Thr Ser Ala Asp Lys Ser Pro Pro
305                 310                 315                 320

Ser Glu Val Val Asp Leu Asp Ala Leu Gln Glu Gln Gln Val Gln Arg
            325                 330                 335

Gln Asp Ser Val Gly Lys Thr Thr Asn Gly Ile Asp Lys Gln Thr Val
            340                 345                 350

Pro Ser Thr Met Asp Leu Leu Gly Val Phe Pro Thr Gly Leu Ala Thr
        355                 360                 365

Ser Thr Pro Glu Thr Asn Thr Ser Gln Ser Gln Gly Ser Ser Asp Ser
        370                 375                 380

Ser Gly Asn Asn Lys Ser Lys Ser His Ser Thr Glu Pro Val Thr Val
385                 390                 395                 400

Val Asn Ser His Asp Lys Ser Thr Arg Asp Phe Ser Ala Ala Gly Phe
            405                 410                 415

Met Arg Ser Asn Ser Thr His Glu Ser Gln Pro His Ile Tyr Lys Gln
            420                 425                 430

Thr Glu Gln Glu Thr Arg Pro Tyr Leu Ser Leu Gln Leu Phe Gly Ser
        435                 440                 445

Thr Glu Glu Asp Phe Pro Pro Lys Met Asp Ser Val Asn Lys Tyr Leu
        450                 455                 460

Ser Ser Glu Ser Ser Asn Pro Leu Asp Glu Arg Ser Pro Ser Ser Ser
465                 470                 475                 480

Pro Pro Ile Thr Arg Lys Phe Phe Pro Ile His Ser Val Asp Glu Glu
            485                 490                 495

Val Arg His Pro His Ile Thr Asp Tyr Gly Glu Asp Ala Thr Met Gly
            500                 505                 510

Glu Val Ser Thr Asn Gln Ala Trp Leu Ala Pro Leu Asp Leu Phe
        515                 520                 525

Lys Asp Ser Glu Arg Pro Ile Glu Asn Gly Ser Pro Asn Pro Gly
530                 535                 540

Tyr Gln Ser Cys Tyr Ala Ser Thr Ser Cys Ser Asp His Ser Pro Ser
545                 550                 555                 560

Thr Ser Asn Ser Asp Gly Gln Asp Arg Thr Gly Arg Ile Ile Phe Lys
            565                 570                 575
```

-continued

```
Leu Phe Gly Lys Glu Pro Ser Thr Ile Pro Gly Asn Leu Arg Asp Asp
            580                 585                 590
Ile Val Asn Trp Leu Lys His Ser Pro Thr Glu Met Glu Gly Tyr Ile
        595                 600                 605
Arg Pro Gly Cys Leu Val Leu Ser Met Tyr Leu Leu Met Pro Gly Ile
    610                 615                 620
Ala Trp Asp Glu Leu Glu Glu Asn Leu Leu Gln Arg Val Asn Ser Leu
625                 630                 635                 640
Val Gln Ser Ser Asp Leu Asp Phe Trp Arg Lys Gly Arg Phe Leu Val
            645                 650                 655
Arg Thr Asn Ser Gln Leu Val Ser Tyr Lys Ala Gly Met Thr Arg Leu
        660                 665                 670
Ser Lys Ser Trp Arg Thr Trp Asn Thr Pro Glu Leu Thr Leu Val Ser
    675                 680                 685
Pro Ile Ala Val Val Gly Gly Gln Lys Thr Ser Leu Ile Leu Lys Gly
690                 695                 700
Arg Asn Leu Ser Ile Pro Gly Thr Gln Ile His Cys Thr Ser Ile Gly
705                 710                 715                 720
Lys Tyr Ile Ser Lys Glu Val Leu Cys Ser Ala Tyr Pro Gly Thr Ile
            725                 730                 735
Tyr Asp Asp Ser Gly Val Glu Thr Phe Asp Leu Pro Gly Gln Pro Asp
        740                 745                 750
Leu Ile Leu Gly Arg Cys Phe Val Glu Val Glu Asn Arg Phe Arg Gly
    755                 760                 765
Asn Ser Phe Pro Val Ile Val Ala Ser Ser Ser Val Cys Gln Glu Leu
770                 775                 780
Arg Asn Leu Glu Val Glu Phe Glu Asp Ser Gln Val Leu Asp Val Ser
785                 790                 795                 800
Ser Asp Gly Gln Ile His Asp Ser Arg Gln Pro Lys Thr Ser Val Gln
            805                 810                 815
Val Leu His Phe Leu Asn Glu Leu Gly Trp Leu Phe Gln Arg Ala Ser
        820                 825                 830
Ala Cys Thr Ser Ser Thr Arg Ser Asp Val Ser Asp Leu Asp Leu Ile
    835                 840                 845
Arg Phe Ser Thr Ala Arg Phe Arg Tyr Leu Leu Leu Phe Cys Ser Glu
850                 855                 860
Arg Asp Trp Cys Ser Leu Thr Lys Thr Leu Leu Asp Ile Leu Ala Lys
865                 870                 875                 880
Arg Ser Leu Ala Ser Glu Glu Leu Ser Lys Glu Thr Met Glu Met Leu
            885                 890                 895
Ala Glu Ile His Leu Leu Asn Arg Ala Val Lys Arg Lys Ser Arg Asn
        900                 905                 910
Met Val His Leu Leu Val Lys Phe Val Ile Cys Pro Asp Asn Ser
    915                 920                 925
Lys Val Tyr Pro Phe Leu Pro Asn Leu Pro Gly Pro Gly Gly Leu Thr
930                 935                 940
Pro Leu His Leu Ala Ala Ser Ile Glu Asn Ala Glu Asp Ile Val Asp
945                 950                 955                 960
Ala Leu Thr Asp Asp Pro Gln Gln Thr Gly Val Thr Cys Trp Gln Thr
            965                 970                 975
Val Leu Asp Asp Asp Gly Gln Ser Pro Glu Thr Tyr Ala Lys Leu Arg
        980                 985                 990
Asn His Asn Ser Tyr Asn Glu Leu Val Ala Gln Lys Leu Val Asp Met
```

```
                 995                1000               1005

Lys Asn Asn Gln Val Thr Val Arg Val Asn Gly Asp Gly Ile Arg Ala
            1010               1015                1020

Asp Arg Leu Gly Asn Asp Val Gly Asp Arg Lys Arg Ser Gly Val Gln
1025                1030               1035                1040

Ala Leu Gln Ile Arg Ser Cys Ser Gln Cys Ala Ile Leu Glu Ser Gly
                1045                1050               1055

Val Leu Met Gln Pro Val Arg Ser Arg Gly Phe Leu Ala Arg Pro Tyr
            1060               1065                1070

Ile His Ser Met Leu Ala Ile Ala Ala Val Cys Val Cys Val Cys Val
            1075               1080               1085

Phe Met Arg Ala Leu Leu Arg Ile Asn Ser Gly Lys Ser Phe Lys Trp
            1090               1095                1100

Glu Arg Leu Asp Tyr Gly Thr Ile
1105               1110

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
tttttttttt ttttt                                                   15

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
atggaggccg ccaggttc                                                18

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
ttacatgggt ccacgctc                                                18

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ctgctctggc cctatttctg                                              20

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide
```

```
-continued

<400> SEQUENCE: 9
gcatcgctcc tcaaggtct                                               19

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 10
acatgcgcct aaggagaaat ag                                           22

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 11
acctccatgc tcactggtac tt                                           22

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
atgcagaggg aggtgggc                                                18

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
ttatattgta ccgtaatcca gc                                           22
```

CORN GENES *ZMSPL1* AND *ZMSPL2* AND USES THEREOF

CROSS-REFERENCE TO RELATED APPLICATIONS

This application is a 35 U.S.C. § 371 national stage filing of International Application No. PCT/CN2013/001475, filed on Nov. 29, 2013, the entire contents of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 23, 2017, is named Seq_Listing_118216_15101 and is 28,186 bytes in size.

TECHNICAL FIELD

The present invention relates to the field of plant transgenetic technology, particularly to corn genes ZmSPL1 and ZmSPL2 and the use of the same.

BACKGROUND OF THE INVENTION

Organ size is an important characteristic of plant morphology. Under the same growth conditions, there is little difference in organ sizes among individuals having the same genotype and within the same species. For different species, the size of seeds and other organs vary greatly, while the individuals belonging to one species have relatively uniform sizes of seeds and other organs of similar size. These facts show that organ size in plants is strictly under genetic control. Meanwhile, the morphogenesis of a plant organ is influenced intensively by the external environment (including factors such as: light, temperature and nutrition). Thus, the mechanism on controlling a plant organ size is very complicated, as is the internal mechanism of a plant which precisely controls the predetermined size of an organ when finally grown. Organ size in a plant is an important yield trait. Thus, an investigation on the sizes of seeds or other organs in a plant will provide a theoretical basis and some novel genetic sources for possible genetic modifications which may be used in developing transgenic high-yield crops.

Plant organ sizes may greatly vary depending on the species. Besides the restrictions of natural conditions, artificial selection has a significant effect in plant organ size. Although the mechanism of organ size self-controlling in a plant is still not clear, there are at least two known potential factors that dominate the organ sizes in a plant, i.e. cell number and cell size. Generally, the size of the same organ in a different species is determined by the cell number therein. However, changing cell number or cell size singly may not always lead to the change of organ size. This is because the variation of one factor may be compensated by other factors. For example, a decrease in cell number of an organ may not lead to a smaller plant organ, because the plant may make up for the decrease of cell number by increasing total cell volume so that the whole organ maintains the same size. Such a coordination mechanism in cell growth suggests an endogenous regulation in the plant itself. Some recent studies have found some critical genes in gene pathways that function to control organ sizes by affecting cell number, cell size or both.

SUMMARY OF THE INVENTION

In one aspect, the present invention provides an isolated nucleic acid molecule comprising a promoter functional in a plant cell positioned to provide for expression of a polynucleotide having the following nucleotide sequence:

(1) a sequence set forth in SEQ ID NO: 1 or 3, or a complementary sequence thereof;

(2) a sequence hybridized with the sequence set forth in SEQ ID NO: 1 or 3 under a stringent hybridization condition;

(3) a sequence having at least 85%, 90%, 91%, 92%, 93%, 94%, 95%, 96%, 97%, 98%, 98.5%, 99%, or 99.5% sequence identity with the sequence set forth in SEQ ID NO: 1 or 3, which encodes a protein exhibiting a function of controlling plant organ sizes; or (4) a sequence obtained from the derivatization of the sequence set forth in SEQ ID NO: 1 or 3 by deletion, substitution, insertion or addition of one or more nucleotides.

In another aspect, the present invention provides an isolated nucleic acid molecule comprising a promoter functional in a plant cell positioned to provide for expression of a polynucleotide having the following nucleotide sequence:

(1) a sequence encoding a polypeptide set forth in SEQ ID NO: 2 or 4;

(2) a sequence encoding a polypeptide having at least 85%, 90%, 91%, 92%, 93%, 94%, 95%, 96%, 97%, 98%, 98.5%, 99%, or 99.5% sequence identity with the sequence set forth in SEQ ID NO: 2 or 4; or (3) a sequence encoding a polypeptide obtained from the sequence set forth in SEQ ID NO: 2 or 4 by deletion, substitution, insertion or addition of one or more amino acids.

In yet another aspect, the present invention provides a recombinant DNA construct comprising the above nucleic acid molecule.

In yet another aspect, the present invention provides an isolated polypeptide, which is selected from the group consisting of:

(1) a polypeptide having the amino acid sequence set forth in SEQ ID NO: 2 or 4; and (2) a polypeptide derived from (1), comprising substitution, deletion, or addition of one or more amino acid residues in the amino acid sequence set forth in SEQ ID NO: 2 or 4 and exhibits a function of controlling plant organ sizes.

In yet another aspect, the present invention provides a plant cell comprising the above nucleic acid molecule, or recombinant DNA construct.

In yet another aspect, the present invention provides a transformed plant comprising the above nucleic acid molecule, or recombinant DNA construct.

In an embodiment according to the aspect of the invention, the transformed plant has an altered trait as compared to a non-transformed plant or wild-type plant, wherein said altered trait is selected from the group consisting of increased seed size, increased seed number, increased seed weight, increased grain size, increased grain number, increased grain weight, increased leaf size, increased leaf area, increased leaf number, increased leaf cell number, increased main root length, increased lateral root number, increased root fresh weight, and increased yield. Overall this can also lead to increased organ size in a plant and/or increased biomass for the plant.

In an embodiment according to the aspect of the invention, the transformed plant is a monocotyledon or dicotyledon plant, preferably a crop plant.

In an embodiment according to the aspect of the invention, the plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

In an embodiment according to the aspect of the invention, the plant is *Arabidopsis thaliana*, rice or corn.

In yet another aspect, the present invention provides the use of the above gene, DNA molecule, recombinant DNA construct or protein in controlling plant organ sizes.

In an embodiment according to the aspect of the invention, said controlling plant organ sizes is increasing plant organ sizes, and the plant organ is a plant seed, leaf or root.

In an embodiment according to the aspect of the invention, the plant is a monocotyledon or dicotyledon plant, preferably a crop plant.

In an embodiment according to the aspect of the invention, the plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

In an embodiment according to the aspect of the invention, the plant is *Arabidopsis thaliana*, rice or corn.

In yet another aspect, the present invention provides a method for breeding a transgenic plant, comprising introducing the above gene into a target plant to obtain a transgenic plant, wherein the transgenic plant has a greater plant organ size than the original target plant.

In an embodiment according to the aspect of the invention, the plant is a monocotyledon or dicotyledon plant, preferably a crop plant.

In an embodiment according to the aspect of the invention, the plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

In an embodiment according to the aspect of the invention, the plant is *Arabidopsis thaliana*, rice or corn.

In an embodiment according to the aspect of the invention, the plant organ is a plant seed, leaf, or root.

In yet another aspect, the present invention provides a method for increasing yield of a plant, wherein said method comprises transforming a plant with the above recombinant DNA construct and obtaining a transformed plant that shows increased yield as compared to a non-transformed plant or wild-type plant.

In an embodiment according to the aspect of the invention, the plant is a monocotyledon or dicotyledon plant, preferably a crop plant.

In an embodiment according to the aspect of the invention, the plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

In an embodiment according to the aspect of the invention, the plant is *Arabidopsis thaliana*, rice or corn.

In yet another aspect, the present invention provides a method for producing a transformed plant having an altered trait, wherein said method comprises transforming a plant with the above recombinant DNA construct and obtaining a transformed plant that shows an altered trait selected from the group consisting of increased seed size, increased seed number, increased seed weight, increased grain size, increased grain number, increased grain weight, increased leaf size, increased leaf area, increased leaf number, increased leaf cell number, increased main root length, increased lateral root number, increased root fresh weight, and increased yield as compared to a non-transformed plant or wild-type plant.

In an embodiment according to the aspect of the invention, the plant is a monocotyledon or dicotyledon plant, preferably a crop plant.

In an embodiment according to the aspect of the invention, the plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

In an embodiment according to the aspect of the invention, the plant is *Arabidopsis thaliana*, rice or corn.

In an embodiment according to the aspect of the invention, the yield is increased by about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100% or more in relative to that of a non-transgenic plant grown under similar conditions. Preferably, said plant is rice and the 1000-weight is increased by 10-25%. Also, preferably, said plant is corn and the 100-weight is increased by 15-25%.

BRIEF DESCRIPTION OF DRAWINGS

FIG. 15 compares the phenotypic characteristics of grains obtained from the ZmSPL1- and ZmSPL2-overexpressed transgenic rice plant and control grains.

FIG. 16 compares the grain length and grain width of the grains obtained from the ZmSPL1- and ZmSPL2-overexpressed transgenic rice and a control plant.

FIG. 17 compares the 1000-grain weight of the grains obtained from the ZmSPL1- and ZmSPL2-overexpressed transgenic rice and a control plant.

FIG. 18 shows the results of PCR identification of transgenic corn seedlings overexpressing ZmSPL1.

FIG. 19 compares the spike traits of a ZmSPL1 overexpressed transgenic corn and the ZHENG-58 corn.

FIG. 20 compares the spike length between ZmSPL1 overexpressed line and Zhen58 control.

FIG. 21 compares the spike width between ZmSPL1 overexpressed line and Zhen58 control.

FIG. 22 compares the spike length between ZmSPL1 overexpressed line and Zhen58 control.

FIG. 23 compares the spike width between ZmSPL1 overexpressed line and Zhen58 control.

FIG. 24 compares the number of grain rows in a spike between ZmSPL1 overexpressed line and Zhen58 control.

FIG. 25 compares the number of grains in a row between ZmSPL1 overexpressed line and Zhen58 control.

FIG. 26 compares the grain size between ZmSPL1 overexpressed line and Zhen58 control.

FIG. 27 compares the 100-grain weight between ZmSPL1 overexpressed line and Zhen58 control.

FIG. 28 compares the grain length between ZmSPL-OX rice and control.

FIG. 29 compares the grain width between ZmSPL-OX rice and control.

FIG. 30 shows the comparison of average grain length.

FIG. 31 shows the comparison of average grain width.

FIG. 32 compares the grain phenotype between ZmSPL1 and ZmSPL2 transgenic rice and control.

FIG. 33 compares the grain length between ZmSPL1 and ZmSPL2 transgenic rice and control.

FIG. 34 compares the grain width between ZmSPL1 and ZmSPL2 transgenic rice and control.

FIG. 35 compares the grain length between ZmSPL-OX rice and control.

FIG. 36 compares the grain width between ZmSPL-OX rice and control.

FIG. 37 shows the comparison of average grain length.

FIG. 38 shows the comparison of average grain width.

FIG. 39 compares the 1000-grain weight between ZmSPL1 and ZmSPL2 overexpressed transgenic rice and control.

DETAILED DESCRIPTION OF THE INVENTION

Figure 1:
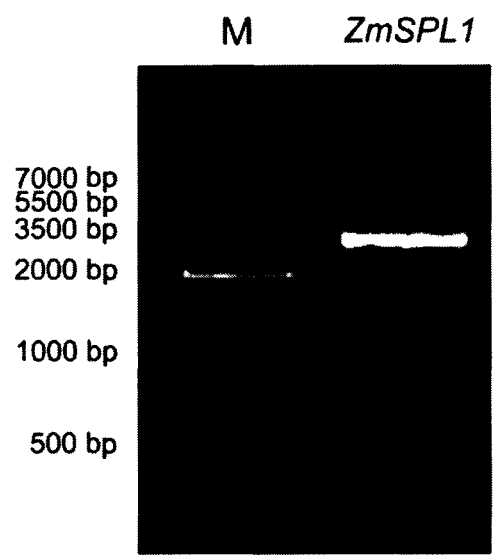
FIG. 1 shows a full length CDS amplification product of the ZmSPL1 gene.

The following definitions and methods are provided to better define the present invention and to guide those of ordinary skill in the art to carry out the present invention. Unless it is specifically pointed out, terms are to be understood according to conventional usage by those of ordinary skill in the relevant art.

As used herein a "plant" includes whole plant, transgenic plant, meritem, shoot organ/structure (for example, leaf, stem and tuber), root, flower and floral organ/structure (for example, bract, sepal, petal, stamen, carpel, anther and ovule), seed (including embryo, endosperm, and seed coat) and fruit (the mature ovary), plant tissue (for example, vascular tissue, ground tissue, and the like) and cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transgenic plant.

As used herein a "control plant" means a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, for example, a wild type plant devoid of a recombinant DNA. A suitable control plant can also be a transgenic plant that contains the recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isoline.

As used herein a "transgenic plant cell" means a plant cell that is transformed with stably-integrated, recombinant DNA, e.g. by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, e.g. into a transgenic plant with stably-integrated, recombinant DNA, or seed or pollen derived from a progeny transgenic plant.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, e.g. by measuring tolerance to water deprivation or particular salt or sugar concentrations, or by the measurement of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance.

As used herein, the term "isolated" refers to at least partially separating a molecule from other molecules normally associated with it in its native or natural state. In one embodiment, the term "isolated gene" or "isolated DNA molecule" refers to a gene or DNA molecule that is at least partially separated from the nucleic acids which normally flank the gene or DNA molecule in its native or natural state. Thus, through for example recombinant technology, genes or DNA molecules fused to regulatory or coding sequences with which they are not normally associated are herein considered isolated. Such molecules are considered isolated even when integrated into the chromosome of a host cell or present in a nucleic acid solution with other DNA molecules.

As used herein, the term "stringency conditions" are those described by Sambrook et al., 1989, and by Haymes et al., In: *Nucleic Acid Hybridization, A Practical Approach*, IRL Press, Washington, D.C. (1985). Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. For example, moderately stringent conditions are at about 2.0×SSC and about 65° C. In one aspect of the present invention, the gene of the present invention has the nucleic acid sequence set forth in SEQ ID NO: 1 or SEQ ID NO: 3. In another aspect of the present invention, the gene of the present invention shares 80%, 81%, 82%, 83%, 84%, 85%, 86%, 87%, 88%, 89%, 90%, 91%, 92%, 93%, 94%, 95%, 96%, 97%, 98%, 98.5%, 99%, and 99.5% sequence identity with the nucleic acid sequence set forth in SEQ ID NO: 1 or SEQ ID NO: 3. In a further aspect of the present invention, the gene of the present invention shares 95% 96%, 97%, 98%, 98.5%, 99%, and 99.5% sequence identity with the sequence set forth in SEQ ID NO: 1 or SEQ ID NO: 3.

The gene of the present invention also comprises a variant sequence derived from the sequence set forth in SEQ ID NO: 1 or SEQ ID NO: 3 via the deletion, substitution, insertion and/or addition of one or more nucleotides. A gene mutation refers to a sudden and inheritable variation of a genomic DNA molecule. In the molecular level, a gene mutation means a change of base pair composition or arrangement sequence in structure. The generation of a gene mutation may be spontaneous or induced. The methods for artificially inducing a gene mutation include physical factors (such as γ ray, x ray, UV, neutron beam and the like), chemical factors (such as an alkylation agent, a base analogue, an antibiotic and the like) and biological factors (such as certain viruses, bacteria, etc.). Furthermore, a specific variation may be introduced at a specified site in a DNA molecule using a recombinant DNA technical so as to carry out a site-directed mutagenesis. Those skilled in the art may use any of these well-known mutagenesis methods to obtain the variant sequence of the sequence set forth in SEQ ID NO: 1 or SEQ ID NO: 3 comprising the deletion, substitution, insertion and/or addition of one or more nucleotides.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that comprises a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the *Arabidopsis thaliana*, corn or rice genome, which may ultimately result in the expression of a recombinant RNA and/or protein molecule in that organism.

As used herein, the term "transgene" refers to a polynucleotide molecule artificially incorporated into a host cell's genome. Such transgene may be heterologous to the host cell. The term "transgenic plant" refers to a plant comprising such a transgene.

As used herein "gene" or "gene sequence" refers to the partial or complete coding sequence of a gene, its complement, and its 5' and/or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the terms "DNA sequence", "nucleotide sequence" and "polynucleotide sequence" refer to the sequence of nucleotides of a DNA molecule, usually presented from the 5' (upstream) end to the 3' (downstream) end.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or a fragment thereof, can also be obtained by other techniques such as by directly synthesizing the fragment by chemical method, such as using an automated oligonucleotide synthesizer.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

As used herein a "polypeptide" comprises a plurality of consecutive polymerized amino acid residues e.g., at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

Recombinant DNA constructs are assembled using methods known to persons of ordinary skill in the art and typically comprise a promoter operably linked to DNA, the expression of which provides the enhanced agronomic trait. Other construct components can include additional regulatory elements, such as 5' leaders and introns for enhancing transcription, 3' untranslated regions (such as polyadenylation signals and sites), and DNA for transit or targeting or signal peptides.

An "isolated polypeptide", whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods.

Percent identity describes the extent to which polynucleotides or protein segments are invariant in an alignment of sequences, for example nucleotide sequences or amino acid sequences. An alignment of sequences is created by manually aligning two sequences, e.g. a stated sequence, as provided herein, as a reference, and another sequence, to produce the highest number of matching elements, e.g. individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

A trait of particular economic interest is increased yield. Yield is normally defined as the measurable production of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and the like may also be important factors in determining yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. The development of a seed involves many genes, and requires the transfer of metabolites from the roots, leaves and stems into the growing seed.

Increased plant biomass encompasses yield for forage crops like alfalfa, silage corn and hay. Many proxies for yield have been used in grain crops. Chief amongst these are estimates of plant or plant organ size. Plant size can be measured in many ways depending on species and developmental stage, but include total plant dry weight, above-ground dry weight, above-ground fresh weight, grain size, grain number, 100- or 1000-grain weight, leaf area, stem volume, plant height, rosette diameter, leaf length, root length, root mass and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679).

With respect to the crops such as maize, rice, etc., the yield means the amount of harvest grains, and the grain size and grain weight traits are key in determining the yield. Thus, increasing grain size and grain weight is an important to increase the yield of a crop.

Controlling of organ size, for example controlling of seed size, especially the controlling of seed size of main crops, is of significant importance in agricultural industry. Organ size is an important yield trait. Thus, the investigation on plant seed size and organ size provides theoretic basis and novel gene sources for high-yield breeding in genetic modification of crops. The present inventors discover new corn ZmSPL1 and ZmSPL2 genes for the first time and they are useful for controlling the size of seed or other organs of corn and other plants (such as *Arabidopsis thaliana*) and the size of rice seed based on phenotypic difference of corn hybrid and parent plants using SSH technique. In the present invention, controlling of organ size means to increase the size of plant organs (e.g. seed, root, leaf, etc.), and the size of the plant organs increases by about 1%-120%, about 10%-110%, about 20%-100%, about 30%-90%, about 40%-80% or about 50%-70%, for example, the size of the plant organs increases by about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 110%, 120% or any value within the above ranges.

SSH is a molecular biological technology for rapidly determining the differential expression between two different biological materials, and it is an effective method for quickly screening differentially expressed genes and it is an important means for finding a new gene. The conditions of the differential genes may be determined by obtaining positive clones through SSH construction, library evaluation and screening (reverse spot hybridization), sequencing the positive clones and performing a bioinformatic analysis. In addition, a full length cDNA sequence may be obtained using the RACE technique and evaluated using Northern blot or Real-time PCR. Through a SSH library analysis on corn Zong31×P138 hybridization embryos, the inventors find out that the expression of corn ZmSPL1 is different between the hybrid and parent plants, which suggests that ZmSPL1 play a role in the embryo development. ZmSPL1 happens to have a high similarity with the longest class of AtSPL in the *Arabidopsis thaliana* sequence. The inventors search the corn DNA database in the MaizeSequence or MaizeGDB corn genome website with tBLASTn against the *Arabidopsis thaliana* AtSPL protein sequences, and use the obtained genomic sequences to search corn EST database with BLASTx and thus the exon regions of the corn genome sequences is deduced and obtained. The longest cDNA sequence (SEQ ID NO: 1) is obtained by manually splicing these sequences. Of course, those skilled in the art can also obtain the cDNA sequence of the ZmSPL1 gene according to the invention using the technologies such as RACE, etc.

*Arabidopsis thaliana* is a small flowering plant that is widely used as a model organism in plant biology including the genetics and plant development studies. *Arabidopsis thaliana* has the same role in the botany as the mouse does in medicine and the *drosophila* in genetics studies. *Arabidopsis thaliana* has the following advantages: a small plant (it is possible to plant several in one cup), a short life cycle (not more than 6 weeks from germination to seed maturation), a high seed production (an individual plant may produce a lot of seeds), and a strong viability (an artificial culture may be obtained on an ordinary culture medium). *Arabidopsis thaliana* has the smallest plant genome known by now. Each haploid chromosome set (n=5) has totally 70 millions of base pairs in length, that is, only ⅟₈₀ of the wheat genome. Thus, it is relatively easier to clone a relevant gene from it. Also, the entire genome of *Arabidopsis thaliana* has been sequenced in 2000, this is the first plant genome subjected to a sequencing analysis. *Arabidopsis thaliana* is a kind of self-pollination plant and is highly homozygous for its genes. And when treated with a physio-chemical factor, it shows a high mutation rate and can readily obtain various plants deficient in metabolism functions. For example, when screening with a medium comprising an herbicide, the anti-herbicide mutation rate is generally obtained at ⅟₁₀₀₀₀₀. Due to the above advantages, *Arabidopsis thaliana* is a better material for genetic studies.

In addition to the classical ABC model in the plant morphogenesis study, in the recent decade, some botanists study similarly on the development of different plant tissues and organs using the *Arabidopsis thaliana* model system. Through analysis of a large number of *Arabidopsis thaliana* mutants, the scientists investigate intensively the development of plant root, stem, leaf, flower, embryo and seed, the mechanisms of disease resistance and stress resistance in plants and the signaling induced by hormones, light and environmental factors involving in various life activities, etc. These extend largely our knowledge on the internal mechanism of life activities in plants.

In order to determine the size of the protein encoded by the presumed gene as well as the locations of start codon and stop codon, the inventors carry out following steps: conducting an open reading frame (ORF) analysis on the presumed cDNA sequence of corn ZmSPL1 gene using the ORF Finder software from NCBI, and determining the correct reading frame with BLASTx. Based on the obtained gene ORF sequence and the corresponding genomic sequence, conducting a structural analysis on the obtained corn ZmSPL1 gene using the gene structural analysis software Gene Structure Display Server.

With the corn B73 genomic map (Schnable, et al., 2009), the inventors locate the obtained sequence on a chromosome and search the upstream sequence in the genome. Specifically, the inventors carry out the following steps: 1) conducting a Genomic BLAST search; 2) observing the genomic structure via "Genome view"; and 3) clicking the corresponding chromosomal regions to locate the position of the gene by the upstream and downstream genes of the corresponding regions.

The inventors further perform a multiple sequence alignment and phylogenetic analysis on the obtained ZmSPL1 gene. In order to analyze the difference between the corn ZmSPL1 gene and the homologous gene sequence in *Arabidopsis thaliana*, the inventors firstly construct a multiple sequence alignment configuration of the SPL sequences using ClusterW (Thompson, et al., 1994) with the default parameters of the software. The inventors introduce the multiple sequence alignment results into GeneDoc, and based on the multiple sequence alignment results of proteins, perform a phylogenetic tree correction using MEGA4.1 (Kumar, et al., 2004) to generate an unrooted phylogenetic tree of the SPL family members of *Arabidopsis thaliana* and corn via neighbor joining.

The inventors investigate the ZmSPL1 gene expression in different plant parts by real-time fluorescence quantitative PCR and find that ZmSPL1 shows significant variations in the expression level between different tissues or organs. The ZmSPL1 gene has the highest expression level in the immature corn ear and tassel, and has a very low expression level in the developing embryo, endosperm, seed coat, root and flower filament.

The inventors further study the function and use of the ZmSPL1 gene. The ZmSPL1 gene according to the invention may be introduced into a plant by various commonly used plant transgenetic methods. For example, *Agrobacterium*-mediated method, gene gun method, PEG-mediated method, ultrasonic method, ovary injection method, pollen-tube pathway method and the like. *Agrobacterium* is a gram-negative bacterium commonly found in soil and can chemotactically infect injured sites of most dicotyledon plants under natural conditions to induce the generation of crown gall and fairy root. Cells of *Agrobacterium tumifaciens* and *Agrobacterium rhizogenes* comprise a Ti plasmid and a Ri plasmid respectively which have a T-DNA segment. After entering plant cells by infecting plant wounds, *Agrobacterium* can insert the T-DNA into the plant genome. Thus, *Agrobacterium* represents a natural plant genetically transformation system. One may insert a target gene into a modified T-DNA region and achieve the transfer and incorporation of an exogenous gene into a plane cell via the *Agrobacterium* infection, then regenerate into a transgenic plant through a cell and tissue culture technology. Initially, the *Agrobacterium*-mediated transformation is only used in dicotyledon plants. In recent years, it is also broadly used in some monocotyledon plants (especially rice). The gene gun-mediated transformation method uses gunpowder explosion or a high-pressure gas to accelerate (this accelerating device is called as a gene gun) micro-projectiles, thereby delivering the high-speed micro-projectiles coated with a target gene into an intact plant tissue and cell, then a transgenic plant is regenerated through a cell and tissue culture technology. The transgene positive plants are screened out, i.e. the transgenic plants. Compared with the *Agrobacterium*-mediated transformation, one main advantage of the gene gun transformation is that it is not restricted by the range of receipt plant. And the construction of its carrier plasmid is relatively simple. Thus, the gene gun transformation is one of the broadly used methods in transgene studies. In the pollen-tube pathway method, a DNA solution containing a target gene is injected into an ovary to introduce an exogenous DNA into a germ cell via a pollen-tube pathway formed during flowering and fertilization of a plant and to further incorporate the exogenous DNA into the genome of the receipt cell, and a new individual plant is grown as the development of the germ cell. The most advantage of this method is its independence of a tissue culture and artificial regeneration technique, and thus this technique is simple, do not need a well-equipped laboratory and is easy to be handled by an ordinary breeding person. The following examples of the invention employ the *Agrobacterium*-mediated transformation method. Specifically, the transformation includes the leaf disc method, the vacuum infiltration method and the protoplast method, etc.

Prior to introduction, it is necessary to construct an expression recombinant vector. There is no limitation on the recombinant vector for introducing into a plant according to the invention. Depending on the introduction and transformation techniques, for example, various plasmids, a Ti plasmid, an artificial chromosome, a plant virus including a RNA virus, a single-strain DNA virus and the like may be used as the vector of the invention. A number of common vector constructing techniques are available now, for example, a conventional vector constructing technique through enzymic cleave of a DNA plasmid. That is, a DNA plasmid is cleaved by a restriction enzyme and then ligate a target gene with a ligase to form an expression vector. This technique has a defect that it need to construct multiple intermediates and thus has a low efficiency. In addition, the Gateway technology developed by the Invitrogen Inc. does not need a restriction enzyme and a ligase. It firstly constructs an entry vector and then repeatedly introduces a target gene into different destination vectors for expression. This method has the characteristics of simplicity, speediness, high cloning efficiency and high specificity (remain the positions of reading frame and gene unchanged). Furthermore, since the antibiotic selection marker gene is a hidden trouble in current transgenic plants, those skilled in the art develop some recombinant vectors without a selection marker and transformation methods thereof, for example, a co-transformation of a binary or ternary expression vector comprising two or three T-DNAs. The following examples of the invention employ the Gateway technology. In order to introducing the ZmSPL1 gene into a plant, the inventors construct an over-expression vector of the ZmSPL1 gene using the Gateway technique. The vector is constructed according to the following procedure: incorporating a gateway BP reaction linker to 5' end of a primer, obtaining the target gene fragments having the linker sequence by PCR amplification, recovering the products via an agarose gel, mixing the recovered products with the vector pDONR221 in a certain ratio, and under the catalysis of BP Clonase™ enzyme, substituting the target gene into the pDONR221 vector. The constructed vector is an entry vector. The inventors mix the constructed entry vector containing the target gene with a destination vector in a certain ratio, and under the catalysis of the LR Clonase™ enzyme, substitute the target gene contained in the entry vector into the destination vector, thereby obtain the overexpression vector containing the target gene. In order to introduce the target gene ZmSPL1 in to a plant such as *Arabidopsis thaliana*, the inventors transform *Agrobacterium tumefaciens* using the constructed overexpression vector. The used *Agrobacterium* may be *Agrobacterium tumefaciens* GV3101 (Ectopic overexpression of wheat TaSrg6 gene confers water stress tolerance in *Arabidopsis*. Tong S M, Ni Z F, Peng H R, Dong G Q, Sun Q X. 2007, 172(6): 1079-1086, available publically from the China Agricultural University). Then the inventors transform Columbia wild type *Arabidopsis thaliana* (col-0, Yao Y, Ni Z, Du J, Han Z, Chen Y, Zhang Q, Sun Q. Ectopic overexpression of wheat adenosine diphosphate-ribosylation factor, TaARF, increases growth rate in *Arabidopsis*. J Integr Plant Biol. 2009, 51(1):35-44, available publically from the China Agricultural University) with competent *Agrobacterium tumefaciens*.

The inventors also perform the phenotypic studies of the *Arabidopsis thaliana* with introduced ZmSPL1 gene (including the development and weight of root system, leaf and seed). The results show that the ZmSPL1-overexpressed *Arabidopsis thaliana* has an increased plant organ (especially seed). Specifically, the inventors perform phenotypic studies of the ZmSPL1 transgenic *Arabidopsis thaliana*, wherein, firstly, the inventors observe microscopically the morphology of *Arabidopsis thaliana* seeds after pollination, and perform a statistic analysis with wild-type *Arabidopsis thaliana* (WT) and empty vector transformed *Arabidopsis thaliana* $T_2$ plant as controls. It can be seen from the results that, compared with the wild-type *Arabidopsis thaliana* seeds, the ZmSPL1 transgenic *Arabidopsis thaliana* (ZmSPL1-OX) are bigger. This mainly manifests in the grain length. Meanwhile, there is no significant difference between the wild-type *Arabidopsis thaliana* (WT) and the empty vector transformed *Arabidopsis thaliana* plant. Also, the inventors investigate the development and weight of seeds. It is found out in the study that a mature *Arabidopsis thaliana* seed mainly consists of an embryo, and the endosperm gradually degrades to disappear as the seed develops. Thus, the inventors further dynamically observe the embryos of seeds 5-9 days after pollination from the ZmSPL1 transgenic *Arabidopsis thaliana* plant (ZmSPL1-OX), the empty vector transformed *Arabidopsis thaliana* plant and the wild-type *Arabidopsis thaliana* plant (WT) by TBO staining (with the same procedure in above). The morphological observations of the embryos after pollination shows that, on day 5 after pollination, when the wild-type seeds are in the early heart stage, the transgenic seeds are still in the globular stage; and on day 9 after pollination, the wild-type seeds may almost fill fully inside the seed coat, but the embryos in the transgenic seeds have much space for development. These results demonstrate that, with the overexpression of ZmSPL1 gene, the development of *Arabidopsis thaliana* seeds shows retardation, thereby leading to a greater storage capacity. Meanwhile, there is no significant difference between the wild-type *Arabidopsis thaliana* (WT) and the empty vector transformed *Arabidopsis thaliana* plant. It can be seen that overexpression of ZmSPL1 may improve the weight. Secondly, the inventors investigate the development of root system of *Arabidopsis thaliana*, wherein a germination test (at 20° C. temperature and a 16 h light/8 h dark photoperiod) is performed on seeds from two plant lines of the ZmSPL1 transgenic *Arabidopsis thaliana* plant (ZmSPL1-OX), the empty vector transformed *Arabidopsis thaliana* plant and the wild-type *Arabidopsis thaliana* plant (WT). The phenotypic results shows that the seeds from the two plant lines of the ZmSPL1 transgenic *Arabidopsis thaliana* plant germinate faster than the wild-type *Arabidopsis thaliana* seeds and have a higher growth rate of the whole root system than the wild-type *Arabidopsis thaliana*. Thirdly, the inventors investigate the leaf size of *Arabidopsis thaliana*, wherein the seeds of ZmSPL1 transgenic *Arabidopsis thaliana* (ZmSPL1-OX), the seeds of empty vector transformed *Arabidopsis thaliana* and the wild-type *Arabidopsis thaliana* seeds (WT) are sowed (at a temperature of 20° C. and a 16 h light/8 h dark photoperiod) and the leaf cells are observed microscopically on day 25. On day 25, the phenotypes of above-ground plant parts are observed. The results show that the above-ground parts of the ZmSPL1 overexpressed plant are larger than those of the wild-type plants. Meanwhile, there is no significant difference between the wild-type *Arabidopsis thaliana* plant (WT) and the empty vector transformed *Arabidopsis thaliana* plant. Through further investigation, the enlargement of above ground parts is found mainly present as an increase of the rosette leaf area. From the microscopic observation of leaf epidermal cells, it is indicated that the leaf is enlarged mainly as a result of the increased cell number instead of the increased cell volume.

Thus, the inventors think the ZmSPL1 gene of the invention plays a role in controlling the organs of *Arabidopsis thaliana* including seed, root system and leaf. The overexpression of ZmSPL1 gene can cause an increase in the weights of the above organs. In the present invention, the size of the plant organs may be increased by about 1%-120%, about 10%-110%, about 20%-100%, about 30%-90%, about 40%-80% or about 50%-70%, for example, the size of the plant organs increases by about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 110%, 120% or any value within the above ranges, such as 115%, 88%, 30%, 24%, or 13%, etc.

In order to further investigate the function and use of the ZmSPL1 gene, the inventors introduce the ZmSPL1 gene into monocotyledon plants rice and corn and study their phenotype. Similarly, the results show that the overexpression of ZmSPL1 gene increases the seed size of rice and corn seeds.

With the same techniques and procedures for the ZmSPL1 gene, the inventors find another ZmSPL2 gene for controlling plants (such as *Arabidopsis thaliana*, corn and rice) from corn and demonstrate by introducing this gene into *Arabidopsis thaliana*, corn and rice that the overexpression of this gene also play a role in controlling plant organs (especially seed size).

The host cells in the invention include, but are not limited to, the bacterial cells for mediating a genetic transformation of a plant, such as *Agrobacterium tumifaciens* cells, and plant cells transformed with a gene.

The plants in the present invention include, but are not limited to, monocotyledon plants and dicotyledon plants, including crop plants (such as corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry, barley, vegetables (such as tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*)), ornamentals (such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*). In a specific embodiment, plants of the present invention are crop plants (for example, corn, alfalfa, sunflower, *Brassica*, soybean, cotton, safflower, peanut, *sorghum*, wheat, millet, tobacco, etc.). In some embodiments, *Arabidopsis thaliana*, rice or corn are preferred.

The following examples are included to demonstrate examples of certain preferred embodiments of the invention. It should be appreciated by those of skilled person in the art that the techniques disclosed in the examples are the best modes of the invention. However, those skilled in the art should, in light of the present disclosure, appreciate that many changes can be made on the specific embodiments as disclosed in the present invention and still a like or similar results can be obtained without departing from the spirit and scope of the invention.

Unless specified otherwise, the experimental methods used in the following examples are conventional ones in the art.

Unless specified otherwise, the materials, reagents used in the following examples are available commercially.

EXAMPLES

Example 1. Acquisition of the Corn ZmSPL1 Gene

1. Finding of the Corn ZmSPL1 Gene
(1) Discovering the Corn ZmSPL1 Gene

Through a SSH library analysis on corn Zong31×P138 hybridization embryos, the inventors find the expression of corn ZmSPL1 between the hybrid and parent plants is different, which suggests ZmSPL1 play a role in the embryo development. ZmSPL1 happens to have a high similarity with the longest class of AtSPL in the *Arabidopsis thaliana* sequence. The inventors search the corn DNA database in the MaizeSequence or MaizeGDB corn genome website with tBLASTn against the *Arabidopsis thaliana* AtSPL protein sequences, and use the obtained genomic sequences to search corn EST database with BLASTx to and the exon regions of the corn genome sequences is deduced. The longest cDNA sequence (SEQ ID NO: 1) is obtained by manually splicing these sequences.

(2) Structural Analysis and Chromosome Location of the Gene

To determine the size of the protein encoded by the presumed gene as well as the locations of start codon and stop codon, the inventors operate as follows: conducting an open reading frame (ORF) analysis on the presumed cDNA sequence of corn ZmSPL1 gene using the ORF Finder software from NCBI, and determining the correct reading frame with BLASTx. Based on the obtained gene ORF sequence and the corresponding genomic sequence, conducting a structural analysis on the obtained corn ZmSPL1 gene using the gene structural analysis software Gene Structure Display Server.

With the corn B73 genomic map (Schnable, et al., 2009), the inventors locate the obtained sequence on a chromosome and search the upstream sequence in the genome. Specifically, 1) conducting a Genomic BLAST search; 2) observing the genomic structure via "Genome view"; and 3) clicking the corresponding chromosomal regions to locate the position of the gene by the upstream and downstream genes of the corresponding regions.

(3) Multiple Sequence Alignment and Phylogenetic Analysis

In order to analyze the difference between the corn ZmSPL1 gene and the homologous gene sequence in *Arabidopsis thaliana*, the inventors firstly construct a multiple sequence alignment configuration of the SPL sequences using ClusterW (Thompson, et al., 1994) with the default parameters of the software. Then, the inventors introduce the multiple sequence alignment results into GeneDoc, and based on the multiple sequence alignment results of proteins, perform a phylogenetic tree correction using MEGA4.1 (Kumar, et al., 2004) to generate an unrooted phylogenetic tree of the SPL family members of *Arabidopsis thaliana* and corn via neighbor joining.

2. Obtaining the Corn ZmSPL1 Gene

From the root material of the corn inbred line zong31 (Yang X, Yan J, Shah T, Warburton M L, Li Q, Li L, Gao Y, Chai Y, Fu Z, Zhou Y, Xu S, Bai G, Meng Y, Zheng Y, Li J. Genetic analysis and characterization of a new maize association mapping panel for quantitative trait loci dissection. Theor Appl Genet. 2010; 121(3):417-31, available publically by the China Agricultural University), RNA was extracted with the Trizol total RNA extraction kit (DP405-01, TIANGEN): the following steps were carried out: adding 1 mL of extraction solution in each tube containing a milled sample and mixing uniformly; after 5 min at room temperature (25° C.), adding 200 µL chloroform, mixing uniformly, and centrifuging (4° C., 12000 rpm) for 15 min; adding an equal volume of isopropanol into the supernatant and leaving for precipitation at room temperature for 30 min; after centrifuging (4° C., 12000 rpm) for 10 min, discarding the supernatant, washing the precipitate with 75% ethanol and then dissolving in 100 µL of DEPC treated double-distilled water. Purifying the crude RNA with $RQ_1$ RNase-Free DNase (M6101, Promega): adding $RQ_1$ reaction solution (100 mM Tris-HCl, 25 mM $MgSO_4$ and 2.5 mM $CaCl_2$, DNAase 10 U) in RNA; after being placed in a 37° C. bath for 30 min, extracting with equal volume of phenol/chloroform; adding two times volume of anhydrous ethanol into the supernatant for precipitation; after centrifuging (4° C., 12000 rpm) for 10 min, discarding the supernatant, washing the precipitate with 75% ethanol and then dissolving in 40 µL of DEPC treated double-distilled water, thereby obtaining the total RNA.

The total reaction system for cDNA synthesis is 20 µL (containing 2 µg of the total RNA, 50 mmol/L of Tris-HCl (pH 8.3), 75 mmol/L of KCl, 3 mmol/L of $MgCl_2$, 10 mmol/L of DTT, 50 µmol/L of dNTPs, 50 µmol of the anchor primer T15: TTTTTTTTTTTTTTT (SEQ ID NO: 5) (TAKARA, D510), 20 U of an RNase Inhibitor (TAKARA, D2313A), 200 U of the M-MLV reverse transcriptase (Promega, M1701)). cDNA was obtained after incubating at 37° C. for 2 hours. 1 µL of cDNA was used in a PCR reaction with the PCR primers: L: ATGGAGGCCGCCAGGTTC (SEQ ID NO: 6), R: TTACATGGGTCCACGCTC (SEQ ID NO: 7).

Referring to the PCR results shown in FIG. 1, a single PCR product by amplification with a specific 3000 bp band was obtained. By sequencing, the gene for encoding the resultant PCR product has the nucleotide sequence as set forth in SEQ ID NO: 1 with a coding region of nucleotides of positions 1-2919 from 5' end to 3' end. This gene is designated as ZmSPL1, and the protein coded by the gene is designated as ZmSPL1 which has the amino acid sequence as set forth in SEQ ID NO: 2.

Sequencing for the specific band (SEQ ID NO: 1) and determining its chromosomal localization, it was found that, said gene is within the 1.11 Bin region on chromosome 1. Next, an analysis on the amino acid sequence of the ZmSPL1-encoded protein was performed, and there is a SBP-box domain at the N-terminal of this sequence. In addition, a homology evaluation analysis was performed on corn and *Arabidopsis thaliana* SPL proteins with the N-J method in MEGA4.1 software.

Figure 2:
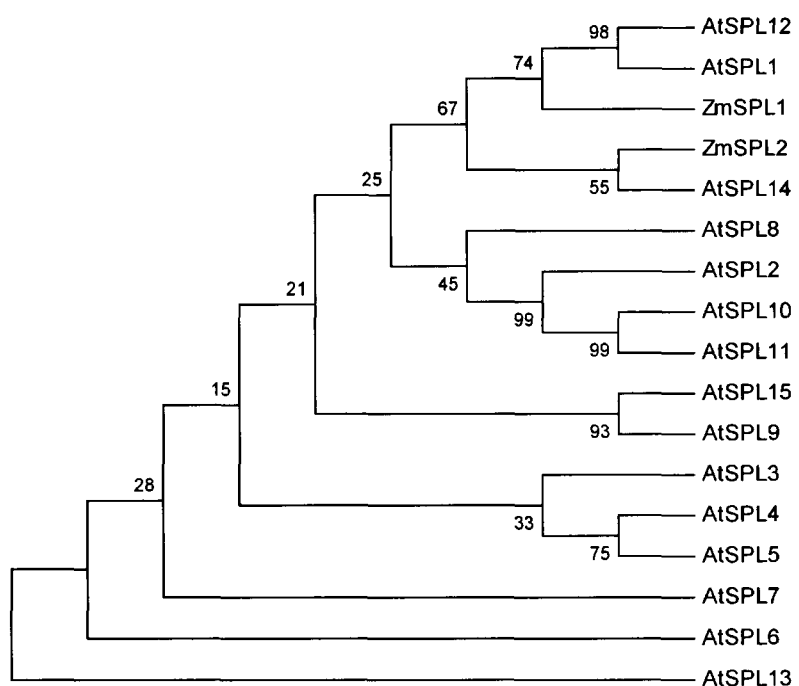
FIG. 2 shows the clustering analysis result of ZmSPL1 and *Arabidopsis thaliana* AtSPL.

The results are shown in FIG. 2, showing that ZmSPL1 is highly similar with a class of SPL coding the longest amino acid sequence (AtSPL1, AtSPL12) in *Arabidopsis thaliana*.

3. Measurement of ZmSPL1 Gene Expression in Different Plant Sites by Real-Time Fluorescence Quantitative PCR The real-time fluorescence quantitative PCR assay was performed on a Bio-Rad C1000 cycler real-time PCR system, and the reaction system of 10 µL contains 1 µL of cDNA, 0.2 µM of real-time quantitative primers and 5 µL of SYBR Premix Ex Taq (DRR041D). The real-time quantitative primers have the following sequences: SPL1-L: CTGCTCTGGCCCTATTTCTG (SEQ ID NO: 8); SPL1-R: GCATCGCTCCTCAAGGTCT (SEQ ID NO: 9). The cDNAs from 11 tissues or organs of corn inbred line Zong31 in different developmental stages were used as templates, i.e. a root and a leaf from a plant of seeding stage (day 8); a stem, an internode, a bracteal leaf, a flower filament, an immature corn ear and tassel from a plant of 60-day growth, and a seed coat, an embryo and an endosperm from a plant 15 days after pollination. The PCR protocol are as follows: denaturating at 94° C. for 5 min; then denaturating at 94° C. for 10 s, annealling at 60° C. for 20 s, and extension at 72° C. for 30 s, 35 cycles; final extension at 72° C. for 7 min. The melting curve was plotted at 65° C.–98° C. Then, a quantitative analysis was performed on the real-time quantitative PCR results using a comparison threshold method with a manually set fluorescence threshold, determining a specific cycle number, Ct value, under such a threshold and calculating the C value for each tissue or organ based on the Ct value, wherein $C=2^{-\Delta Ct}$, and $\Delta Ct=Ct_{target\ gene}-Ct_{internal\ standard}$. A significance test was performed with the two-tail equal variance t test (p<0.05). This experiment include 3 biological repeats.

With the corn 18S rRNA gene as a control, the primer sequences are L: ACATGCGCCTAAGGAGAAATAG (SEQ ID NO: 10); R: ACCTCCATGCTCACTGGTACTT (SEQ ID NO: 11).

Figure 3:
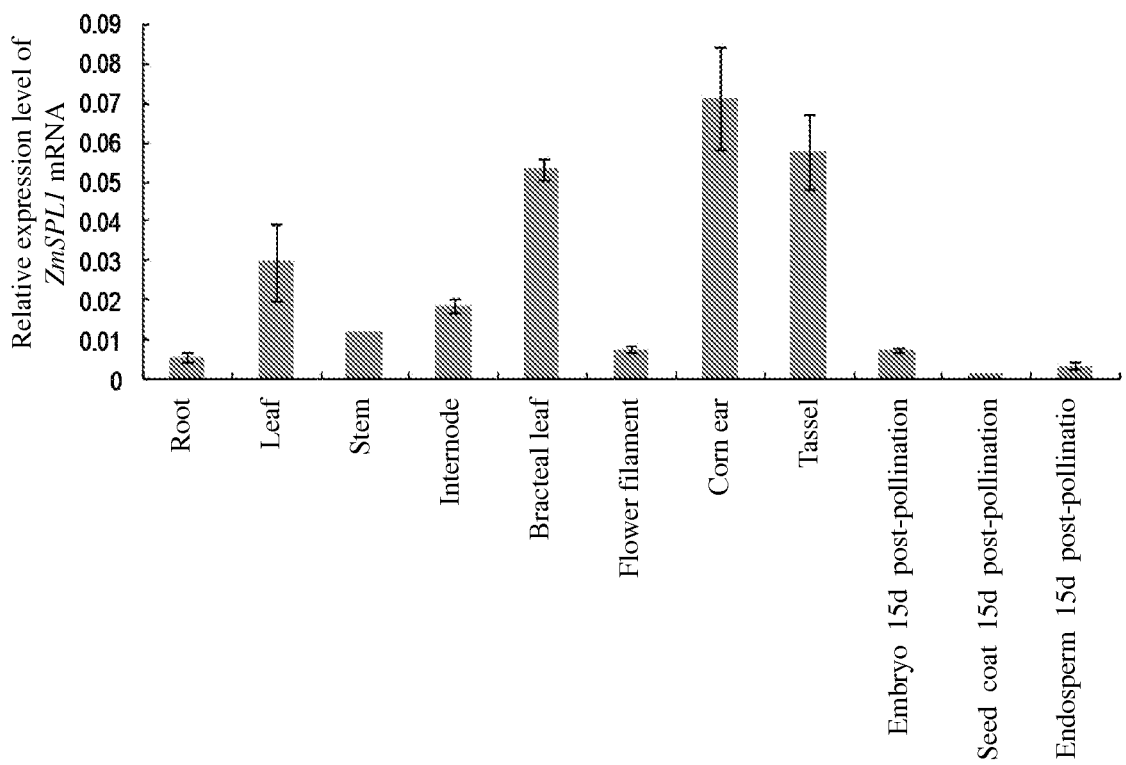
FIG. 3 shows the expression of ZmSPL1 gene in different corn tissues.

According to the results as shown in FIG. 3, ZmSPL1 shows significant variations in the expression level between different tissues or organs. The ZmSPL1 gene has the highest expression level in the immature corn ear and tassel, and has a very low expression level in the developing embryo, endosperm, seed coat, root and flower filament.

Example 2. Use of the ZmSPL1 Gene

Through the Gateway technique, an overexpression vector of the corn ZmSPL1 gene was constructed. The *E. coli* strain is DH5a and the *Agrobacterium* strain is GV3101.

1. Construction of the Overexpression Vector

Through the Gateway technique, the vector was constructed according to the following procedures: incorporating a gateway BP reaction linker to 5' end of a primer, obtaining the target gene fragments having the linker sequence by PCR amplification, recovering the products via a agarose gel, mixing the recovered products with the vector pDONR221 in a certain ratio, and under the catalysis of BP Clonase™ enzyme, substituting the target gene into the pDONR221 vector. The constructed vector is an entry vector. Then, the follows steps were taken: mixing the constructed entry vector containing the target gene with a destination vector in a certain ratio, and under the catalysis of the LR Clonase™ enzyme, substituting the target gene contained in the entry vector into the destination vector, thereby obtaining the overexpression vector containing the target gene.

(1) BP Reaction

BP reaction system:

| | |
|---|---|
| The PCR product obtained form step 2 of example 1 (100 fmol) | 3.5 ul |
| pDONR ™ vector (Invitrogen, 12536-017), 50 ng/ul) | 0.5 ul |
| BP Clonase ™ enzyme mixture (Invitrogen, 11789-013) | 1.0 ul |
| To a total volume | 5.0 ul |

Warming the reaction in a bath of 25° C. for 16 h.

Screening and Identification of BP Reaction Target Gene Clones a. transforming competent cells of *E. coli* DH5α with 2 ul of the BP reaction products, and culturing invertedly at 37° C. for 16 h (in a kan resistive culture medium);

b. picking up a single clone, and culturing at 37° C. with shaking at 200 rpm (adding 50 ug/ml Kan);

c. extracting plasmids, and amplifying with the gene specific primers L: ATGGAGGCCGCCAGGTTC (SEQ ID NO: 6) and R: TTACATGGGTCCACGCTC (SEQ ID NO: 7) to obtain an amplification product;

d. sequencing for the amplification product and comparing with the original sequence. The plasmid whose amplification product has the sequence of SEQ ID NO: 1 is the entry vector BP plasmid.

(2) LR Reaction

Performing an LR reaction using the obtained entry vector of the corn ZmSPL1 gene with a reaction system as below:

| | |
|---|---|
| The BP plasmid obtained from the above step (1) (100 fmol) | 3.5 ul |
| The destination vector pB2GW7 (Invitrogen, 11791019, 150 ng/ul) | 0.5 ul |
| LR Clonase ™ enzyme mixture | 1.0 ul |
| To a total volume | 5.0 ul |

Warming in a bath of 25° C. for 16 h.

Screening and Identification of LR Reaction Target Gene Clones (1) transforming competent cells of *E. coli* DH5α with 2 ul of the LR reaction products, and culturing invertedly at 37° C. for 12-16 h (in a spectinomycin resistive culture medium);

(2) picking up a single clone, and culturing at 37° C. with shaking at 180-200 rpm (adding 50 ug/ml spectinomycin);

(3) extracting plasmids, and amplifying with the gene specific primers L: ATGGAGGCCGCCAGGTTC (SEQ ID NO: 6) and R: TTACATGGGTCCACGCTC (SEQ ID NO: 7) to obtain an amplification product.

Sequencing for the amplification product. The plasmid having the sequence of SEQ ID NO: 1 is the overexpression vector which is obtained by inserting the sequence of SEQ ID NO: 1 into the pB2GW7 plasmid with the Gateway™ technique. This plasmid is designated as pB2GW7-ZmSPL1.

2. Preparation of the ZmSPL1 Transgenic *Arabidopsis thaliana*

(1) Preparation of *Agrobacterium* Competent Cells a. Picking up a single colony of *Agrobacterium tumefaciens* GV3101 (Ectopic overexpression of wheat TaSrg6 gene confers water stress tolerance in *Arabidopsis*. Tong S M, Ni Z F, Peng H R, Dong G Q, Sun Q X. 2007, 172(6): 1079-1086, available publically from the China Agricultural University) in 3 ml of YEB liquid medium (containing a corresponding antibiotic, 100 µg/ml Rif), and culturing with shaking at 28° C. overnight;

b. Inoculating 500 µl of the overnight cultured bacterial liquid in 50 ml YEB liquid medium (containing a corresponding antibiotic), and culturing with shaking at 28° C. until reaching $OD_{600}$ of 0.5;

c. centrifuging at 5000 rpm for 5 min;

d. adding 10 ml of 0.15 mmol/L NaCl to suspend the *agrobacterium* cells, and centrifuging at 5000 rpm for 5 min;

e. suspending the cells in 1 ml of precooled 20 mmol/L $CaCl_2$, and storing in an ice bath until use within 24 h, or subdividing into 200 µl/tube; quick freezing in liquid nitrogen for 1 min, and storing under −80° C. until use.

(2) Preparation and Identification of Positive *Agrobacterium* Clones a. slowly thawing 200 µl of competent cells on ice for 30 min;

b. adding 1 µg of the constructed plasmid pB2GW7-ZmSPL1, and placing on ice for 30 min;

c. quick freezing in liquid nitrogen for 2 min, placing in a water bath of 37° C. for 5 min and on ice for 2 min;

d. then adding into 1 ml YEB culture medium, and culturing with shaking slowly at 28° C. for 4 h;

e. centrifugating at 4000 rpm for 5 min, and discarding the supernatant 900 µl;

f. spreading the remaining liquid on a YEB plate containing 50 µg/ml of spectinomycin and 100 µg/ml of Rif, and culturing at 28° C. for 2 days;

g. picking up a single colony grown on the plate, inoculating in a YEB liquid medium (containing 50 µg/ml of spectinomycin and 100 µg/ml of Rif) in a ratio of 1:50, and culturing with shaking at 28° C. overnight.

Extracting the plasmid from recombinant bacteria and amplifying with the gene specific primers L: ATGGAGGCCGCCAGGTTC (SEQ ID NO: 6) and R: TTACATGGGTCCACGCTC (SEQ ID NO: 7) to obtain a 3000 bp product, which is a positive recombinant bacteria and it is designated as GV3101/pB2GW7-ZmSPL1.

(3) Transformation of *Arabidopsis thaliana* a. vernalizing the seeds of Columbia wild type *Arabidopsis thaliana* (col-0, Yao Y, Ni Z, Du J, Han Z, Chen Y, Zhang Q, Sun Q. Ectopic overexpression of wheat adenosine diphosphate-ribosylation factor, TaARF, increases growth rate in *Arabidopsis*. J Integr Plant Biol. 2009, 51(1):35-44, available publically from the China Agricultural University) (hereinafter referred to as wild-type *Arabidopsis thaliana*) at 4° C. for 72 h, sowing in a MS culture medium and cultivating at 20° C. in a cultivation chamber of 60% humidity at a 16 h light/8 h dark photoperiod; after growing with two true leaves, transplanting the seedlings in a planting bowl containing a mixture of a nutrient soil and vermiculite in an equal ratio.

b. after flowering, cutting the tip of bough to facilitate the development of lateral branches. Within 6 days after pruning, preparing the plant for *agrobacterium* transformation;

c. inoculating the *agrobacterium* GV3101/pB2GW7-Zm-SPL1 in a culture medium containing 5 ml YEB+100 μg/ml SP+100 μg/ml Rifampin, culturing with shaking for overnight, and transferring to 500 ml YEB liquid medium the next day for culturing at 28° C. until to $OD_{600}$ of about 0.8;

d. collecting thallus by configuration, and suspending the *agrobacterium* bacteria in a transformation buffer. 4 days after pruning, dipping the plants in the transformation buffer invertedly;

e. taking the planting plate and encasing with a black plastic bag filled with air, placing horizontally; after cultivating at 20° C. in dark for 24 h, removing the plastic bag and standing the planting bowl upright. Cultivating the plants under normal light and temperature conditions until seeding. Harvesting the mature $T_0$ seeds of the ZmSPL1 transgenic *Arabidopsis thaliana*.

(4) Screening Positive Seedlings of Transgenic *Arabidopsis thaliana*

Preparing an MS plate, sterilizing the $T_0$ seeds of ZmSPL1 transgenic *Arabidopsis thaliana* prior to washing 6 times with sterile water; spreading the seeds on a selective MS culture medium (125 μL/L Basta), after vernalizing at 4° C. for 3 days, transferring to a green house at 20° C. and a 16 h light/8 h dark photoperiod and selecting the positive plants after 7-day cultivation. The positive plants have the following characteristics: healthy true leaf in dark green color and roots stretching into the culture medium.

Extracting genomic DNA from the positive plants obtained through the above primary screen, amplifying with the gene specific primers L: ATGGAGGCCGCCAGGTTC (SEQ ID NO: 6) and R: TTACATGGGTCCACGCTC (SEQ ID NO: 7) to obtain a 3000 bp product, which means that it is a positive $T_0$ plant of ZmSPL1 transgenic *Arabidopsis thaliana*. In total 90 positive $T_0$ plants of ZmSPL1 transgenic *Arabidopsis thaliana* were obtained.

Transferring the above positive $T_0$ plants of ZmSPL1 transgenic *Arabidopsis thaliana* to a normal culture medium, transplanting into soil after 10 days, and harvesting $T_1$ seeds after 50-day growth. Cultivating and screening the $T_1$ seeds in a same method, transplanting and harvesting $T_2$ seeds in a segregation ratio of 3:1 from individual plants. Cultivating 10 plants for each $T_2$ plant line and screening in a same manner to obtain pure line without segregation, thereby the ZmSPL1 transgenic *Arabidopsis thaliana* $T_2$ plants were obtained.

Similarly, transforming the empty vector pB2GW7 into the wild-type *Arabidopsis thaliana* to obtain empty vector transformed *Arabidopsis thaliana* $T_0$ plants. Extracting RNA, preparing cDNA through reverse transcription, and amplifying with the gene specific primers L: ATGGAGGCCGCCAGGTTC (SEQ ID NO: 6) and R: TTACATGGGTCCACGCTC (SEQ ID NO: 7). No target fragment was obtained, which means that it is a positive empty vector transformed *Arabidopsis thaliana*. Similarly, after harvesting and sowing, the empty vector transformed *Arabidopsis thaliana* $T_2$ plants were finally obtained.

3. Phenotypic Studies of the ZmSPL1 Transgenic *Arabidopsis thaliana*

1) Seed Study (1) Microscopic Observation on the Morphology of *Arabidopsis thaliana* Seeds after Pollination a. placing the $T_2$ seeds of ZmSPL1 transgenic *Arabidopsis thaliana* (ZmSPL1-OX) 7 days after pollination in a 50% FAA fixation liquid until use.

b. removing the seeds from the FAA fixation liquid and pacing serially in 70%, 85% and 95% ethanol each for 30 min, then transferring into 100% ethanol for dehydration 3 times, each for 1 h, and overnight for the last time.

c. next day, placing the seeds in a mixture of 100% ethanol and wintergreen oil (1:1) for 1 h, then transferring into wintergreen oil for clarifying 3 times, each for 1 h, and over 1 day for the last time.

d. toluidine blue staining: staining in a toluidine blue working liquid for 3 minutes, color separating in 95% alcohol for 1 minute, two times, dehydrating in 100% alcohol and clarifying in wintergreen oil.

e. mounting with Canadian resin, and after drying, observing the shape and contour of lodicule as well as the central cell structure on a Nikon Ti differential interference contrast microscope and taking pictures.

Wild-type *Arabidopsis thaliana* (WT) and empty vector transformed *Arabidopsis thaliana* $T_2$ plant were used as controls, 30 seeds for each plant line were evaluated, the experiment were repeated three times, and the results were averaged out.

Figure 4:
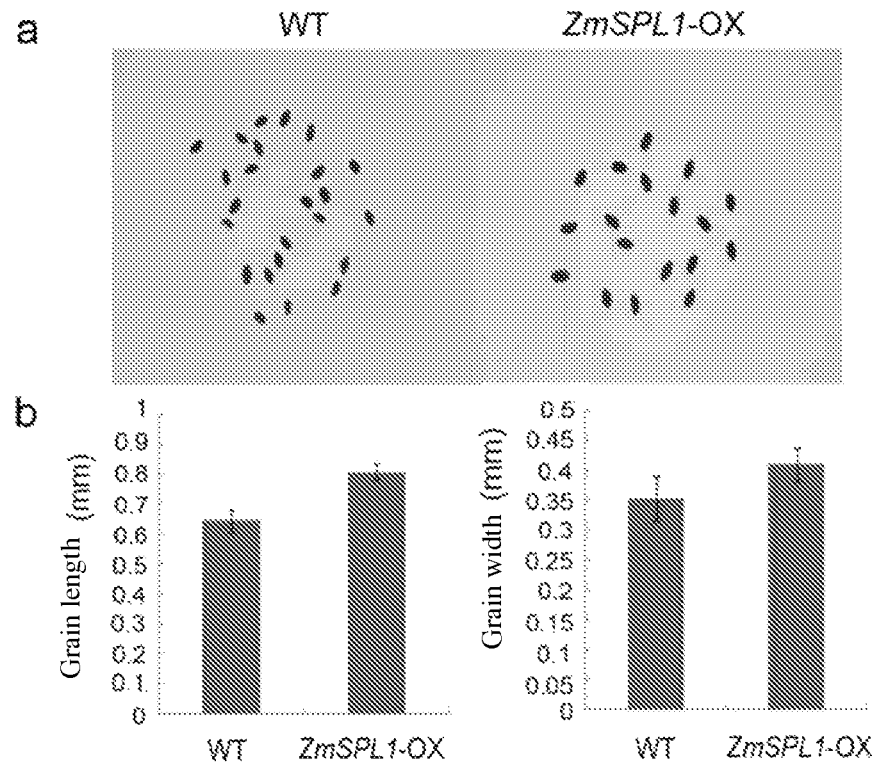
FIG. 4 shows the phenotypic characteristics of seeds in a ZmSPL1-overexpressed transgenic *Arabidopsis thaliana*.

The results are shown in FIG. 4a. It can be seen that, compared to the wild-type *Arabidopsis thaliana* seeds, the $T_2$ seeds of ZmSPL1 transgenic *Arabidopsis thaliana* (ZmSPL1-OX) are bigger. This mainly manifests in the grain length (under a magnification of 11.5 of the microscope).

The grain length and grain width statistically were quantified. According to the results shown in FIG. 4b, the $T_2$ seeds of ZmSPL1 transgenic *Arabidopsis thaliana* (ZmSPL1-OX) and the wild-type *Arabidopsis thaliana* seeds (WT) have a grain length of 0.809 and 0.645 mm respectively, and a grain width of 0.4103 and 0.352 mm respectively.

There is no significant difference between the wild-type *Arabidopsis thaliana* (WT) and the empty vector transformed *Arabidopsis thaliana* $T_2$ plant.

(2) Seed Development and Seed Weight

A mature *Arabidopsis thaliana* seed has been found mainly consisting of an embryo, and the endosperm gradually degrades to disappear as the seed develops. Thus, the inventors further dynamically observed the embryos of seeds 5-9 days after pollination from the ZmSPL1 transgenic *Arabidopsis thaliana* $T_2$ plant (ZmSPL1-OX), the empty vector transformed *Arabidopsis thaliana* $T_2$ plant and the wild-type *Arabidopsis thaliana* plant (WT) by TBO staining (with the same procedure in above step (1)).

Figure 5:
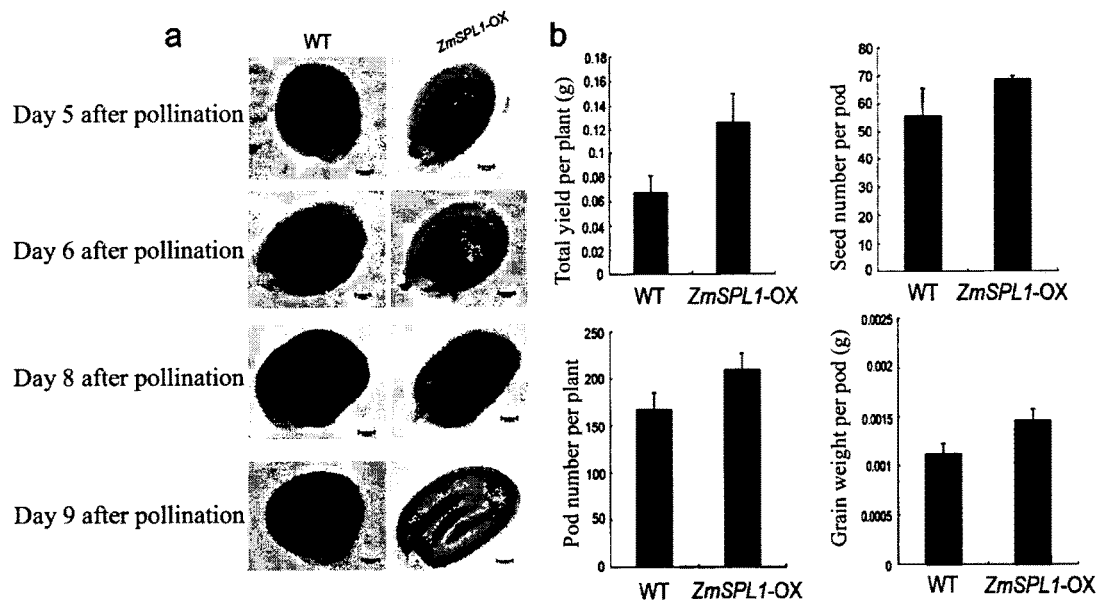
FIG. 5 shows the phenotypic characteristics of seeds and embryos after pollination in a ZmSPL1-overexpressed transgenic *Arabidopsis thaliana* and a wild-type plant.

The morphological observations of the embryos after pollination are shown in FIG. 5a. On day 5 after pollination, when the wild-type seeds are in the early heart stage, the transgenic seeds are still in the globular stage; and on day 9 after pollination, the wild-type seeds almost fill fully inside the seed coat, but the embryos in the transgenic seeds still had much space for development. These results demonstrate that, with the overexpression of ZmSPL1 gene, the development of *Arabidopsis thaliana* seeds shows retardation, therefore there is a greater storage capacity in the seeds.

FIG. 5b shows the statistic results of yields, 3 plants for each plant line, and the experiment were repeated 3 times. The results were averaged out.

The results show that:

For the ZmSPL1 transgenic *Arabidopsis thaliana* $T_2$ plant (ZmSPL1-OX) and the wild-type *Arabidopsis thaliana* plant (WT), the total yield per plant is 0.1256 and 0.0669 g respectively;

For the ZmSPL1 transgenic *Arabidopsis thaliana* $T_2$ plant (ZmSPL1-OX) and the wild-type *Arabidopsis thaliana* plant (WT), the number of seeds per pod is 68.67 and 55.5 respectively;

For the ZmSPL1 transgenic *Arabidopsis thaliana* T$_2$ plant (ZmSPL1-OX) and the wild-type *Arabidopsis thaliana* plant (WT), the pods number per plant is 209.857 and 167.3 respectively;

For the ZmSPL1 transgenic *Arabidopsis thaliana* T$_2$ plant (ZmSPL1-OX) and the wild-type *Arabidopsis thaliana* plant (WT), the grain weight per pod is 0.001467 and 0.001125 g respectively.

There is no significant difference between the wild-type *Arabidopsis thaliana* plant (WT) and the empty vector transformed *Arabidopsis thaliana* T$_2$ plant.

So, it can be seen that overexpression of ZmSPL1 may increase the weight.

2) Development of Root System

A germination test (at 20° C. temperature and a 16 h light/8 h dark photoperiod) on seeds from two plant lines ZmSPL1-OX-1 and ZmSPL1-OX-2 of the ZmSPL1 transgenic *Arabidopsis thaliana* T$_2$ plant (ZmSPL1-OX), the empty vector transformed *Arabidopsis thaliana* T$_2$ plant and the wild-type *Arabidopsis thaliana* plant (WT) was performed.

Figure 6:
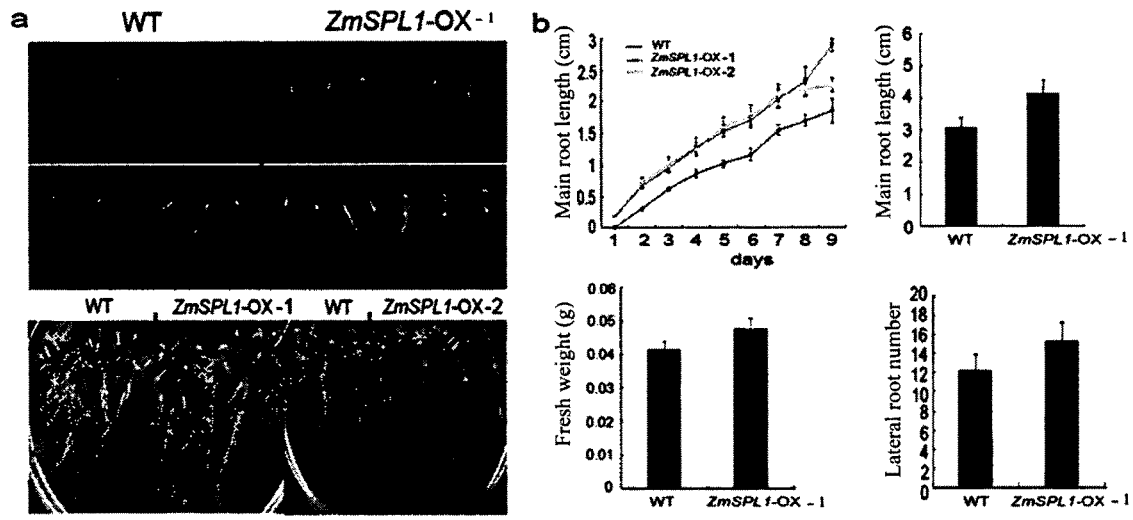
FIG. 6 shows the phenotypic characteristics of root system in a ZmSPL1-overexpressed transgenic *Arabidopsis thaliana*.

The phenotypic results are shown in FIG. 6a, in which the three rows in the figure represent the results obtained on day 2, 7 and 14 after sowing. It can be seen that the ZmSPL1-OX-1 and ZmSPL1-OX-2 seeds germinate faster than the wild-type *Arabidopsis thaliana* seeds and have a higher growth rate of the whole root system than the wild-type *Arabidopsis thaliana*.

The main root length, the number of lateral roots and root fresh weight statistically were quantified. 3 plants for each plant line, and repeating the experiment 3 times. The results were averaged out.

The results are shown in FIG. 6b (the main root length on day 14 is not shown).

On day 1-9, ZmSPL1-OX-1 has a main root length of 0.168125, 0.675833, 0.950833, 1.258889, 1.53125, 1.705, 2.041667, 2.329167 and 2.9 cm respectively; On day 1-9, ZmSPL1-OX-2 has a main root length of 0.145, 0.68, 1.01, 1.16667, 1.525, 1.6667, 2.125, 2.65 and 3.2 cm respectively;

On day 1-9, WT has a main root length of 0, 0.305, 0.620833, 0.866667, 1.016667, 1.155556, 1.544, 1.7 and 1.85 cm respectively;

On day 14, ZmSPL1-OX-1 and WT has a main root length of 4.15 and 3.09 cm respectively;

On day 14, ZmSPL1-OX-1 and WT has a total root fresh weight of 0.0477 and 0.0415 g respectively;

On day 14, ZmSPL1-OX-1 and WT has a lateral root number of 15.33 and 12.17 respectively.

There is no significant difference between the wild-type *Arabidopsis thaliana* plant (WT) and the empty vector transformed *Arabidopsis thaliana* T$_2$ plant.

So, it can be seen that overexpression of ZmSPL1 increases the main root length, the lateral root number and the root fresh weight.

3) Leaf

Sowing the T$_2$ seeds of ZmSPL1 transgenic *Arabidopsis thaliana* (ZmSPL1-OX), the T$_2$ seeds of empty vector transformed *Arabidopsis thaliana* and the wild-type *Arabidopsis thaliana* seeds (WT) (at a temperature of 20° C. and a 16 h light/8 h dark photoperiod).

Meanwhile, observing the leaf cells microscopically on day 25 according to the following specific procedure:

a) boiling fresh leaves of *Arabidopsis thaliana* in water to kill cells, then pouring out the water with dissolved pigments;

b) transferring the material into 95% ethanol, and boiling until the tissue discolor completely (about 1 hour);

c) placing the still warm, discolored material into 85% lactic acid preheated to 96° C., and obtaining transparent tissue material after 8 minutes;

d) transferring the transparent material in 85% lactic acid at room temperature and storing until used for mounting;

e) mounting and observing: taking the *Arabidopsis thaliana* leaves treated for transparency and sucking excess lactic acid with an absorbent paper, then mounting with ethylene glycol and observing under a microscope.

Figure 7:
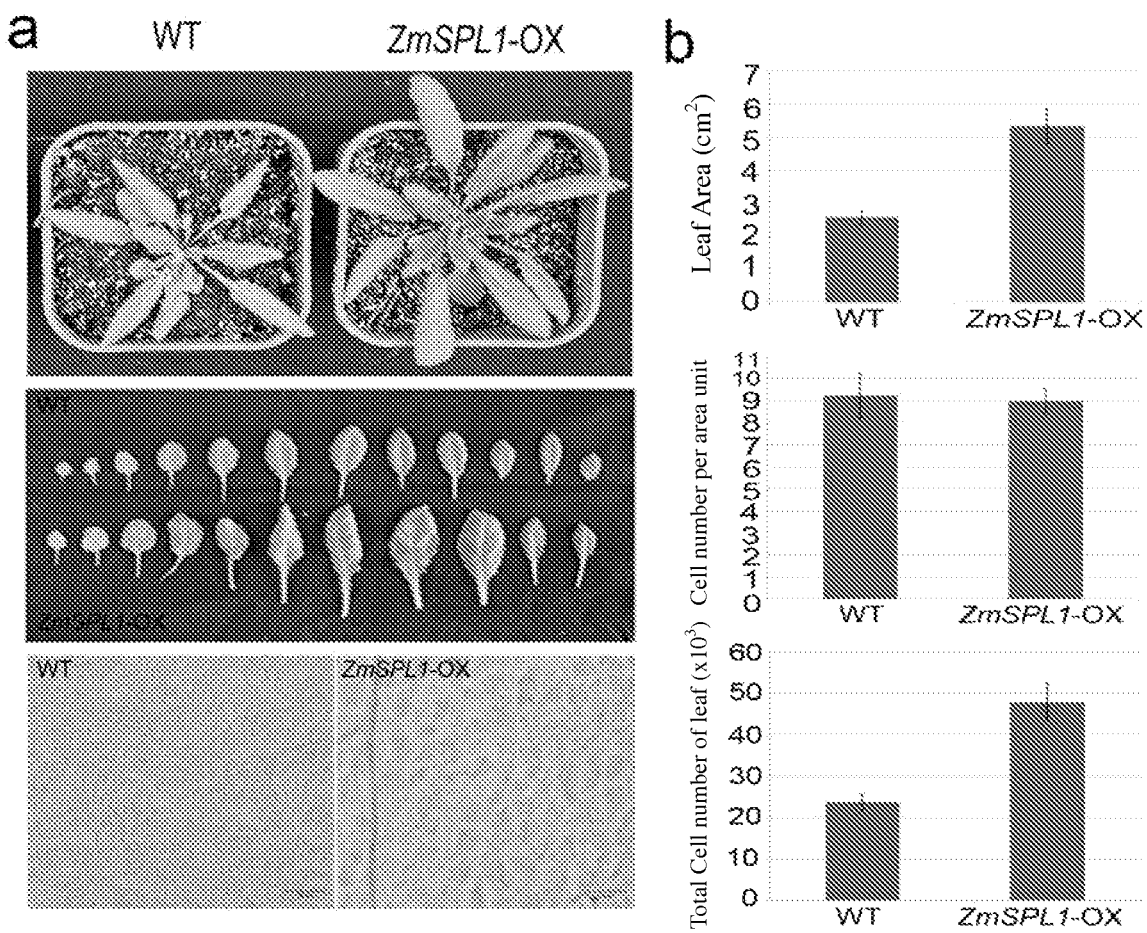
FIG. 7 shows the phenotypic characteristics of leafs in a ZmSPL1-overexpressed transgenic *Arabidopsis thaliana* and a wild-type plant.

On day 25, investigating the phenotypes of above-ground plant parts. The results are shown in FIG. 7a, wherein the first, second and third row represent the above-ground parts, rosette leaf and leaf cells of the wild-type and ZmSPL1 transgenic *Arabidopsis thaliana* on day 25. It can be seen that the above-ground parts of the ZmSPL1 overexpressed plant are larger than those of the wild-type plants.

Quantifying the leaf area, leaf number and leaf cell number of rosette leaf on day 25 statistically. The measurement of leaf area may be carried out through any conventional method known in the art, such as the grid-point method, graph paper method, and paper weighing method, or leaf area may be measured with a leaf area meter such as LAI-3100 area meter from LI-COR. Some leaf area prediction models are also useful in measurement of leaf area (see, e.g., Sezer I, Oner F, Mut Z., Non-destructive leaf area measurement in maize (*Zea mays* L.), J Environ Biol. 2009 September; 30 (5 Suppl): 785-90). The leaf number may be determined by direct counting or may be estimated according to single-side leaf vein number. The leaf cell number may be measured by the flow cytometry which is well-known in the art. 3 plants are measured for each plant line, and the experiment is repeated for 3 times. The results are averaged out.

The results are shown in FIG. 7b.

For the ZmSPL1 transgenic *Arabidopsis thaliana* T$_2$ plant (ZmSPL1-OX) and the wild-type *Arabidopsis thaliana* plant (WT), the leaf area of rosette leaf is 5.338 and 2.558 cm$^2$ respectively;

For the ZmSPL1 transgenic *Arabidopsis thaliana* T$_2$ plant (ZmSPL1-OX) and the wild-type *Arabidopsis thaliana* plant (WT), the cell number per area unit of rosette leaf is 8.98 and 9.23 respectively;

For the ZmSPL1 transgenic *Arabidopsis thaliana* T$_2$ plant (ZmSPL1-OX) and the wild-type *Arabidopsis thaliana* plant (WT), the leaf cell number of rosette leaf is 47.94×10$^3$ and 23.61×10$^3$ respectively.

There is no significant difference between the wild-type *Arabidopsis thaliana* plant (WT) and the empty vector transformed *Arabidopsis thaliana* T$_2$ plant.

Through further investigation, the enlargement of above ground parts is found mainly caused by an increase of the rosette leaf area. Through the microscopic observation of leaf epidermal cells, it was found out that the leaf is enlarged mainly as a result of the increased cell number instead of the increased cell volume.

Example 3. Acquisition of the Corn ZmSPL2 Gene

1. Finding of the Corn ZmSPL2 Gene (1) Discovering the Corn ZmSPL2 Gene

Through a SSH library analysis on corn Zong31×P138 hybridization embryos, the inventor found out that there is a difference in expression of corn ZmSPL2 between the hybrid and parent plants, which suggests that ZmSPL2 plays a role in the embryo development. ZmSPL2 happens to have a high similarity with the longest class of AtSPL in the *Arabidopsis thaliana* sequence. The follows steps were taken: searching the corn DNA database in the MaizeSequence or MaizeGDB corn genome website with tBLASTn against the *Arabidopsis thaliana* AtSPL protein sequences, and using the obtained genomic sequences to search corn EST database with BLASTx and the exon regions of the corn genome sequences was deduced. The longest cDNA sequence (SEQ ID NO: 3) was obtained by manually splicing these sequences.

(2) Structural Analysis and Chromosome Location of the Gene

To determine the size of the protein encoded by the presumed gene as well as the locations of start codon and stop codon, an open reading frame (ORF) analysis on the presumed cDNA sequence of corn ZmSPL2 gene using the ORF Finder software from NCBI was conducted, and the correct reading frame with BLASTx was determined. Based on the obtained gene ORF sequence and the corresponding genomic sequence, a structural analysis on the obtained corn ZmSPL2 gene was conducted using the gene structural analysis software Gene Structure Display Server.

With the corn B73 genomic map, the obtained sequence was located on a chromosome and the upstream sequence in the genome was searched. Specifically, the following steps were taken: 1) conducting a Genomic BLAST search; 2) observing the genomic structure via "Genome view"; and 3) clicking the corresponding chromosomal regions to locate the position of the gene by the upstream and downstream genes of the corresponding regions.

(3) Multiple Sequence Alignment and Phylogenetic Analysis

In order to analyze the difference between the corn ZmSPL2 gene and the homologous gene sequence in *Arabidopsis thaliana*, the inventors firstly constructed a multiple sequence alignment configuration of the SPL sequences using ClusterW (Thompson, et al., 1994) with the default parameters of the software. Then, the following steps were taken: introducing the multiple sequence alignment results into GeneDoc, and based on the multiple sequence alignment results of proteins, performing a phylogenetic tree correction using MEGA4.1 (Kumar, et al., 2004) to generate an unrooted phylogenetic tree of the SPL family members of *Arabidopsis thaliana* and corn via neighbor joining.

2. Obtaining the Corn ZmSPL2 Gene

From the root material of the corn inbred line zong31 (Yang X, Yan J, Shah T, Warburton M L, Li Q, Li L, Gao Y, Chai Y, Fu Z, Zhou Y, Xu S, Bai G, Meng Y, Zheng Y, Li J. Genetic analysis and characterization of a new maize association mapping panel for quantitative trait loci dissection. Theor Appl Genet. 2010; 121(3):417-31, available publically by the China Agricultural University), RNA was extracted with the Trizol total RNA extraction kit (DP405-01, TIANGEN): and the following steps were taken: adding 1 mL of extraction solution in each tube containing a milled sample and mixing uniformly; after 5 min at room temperature (25° C.), adding 200 µL chloroform, mixing uniformly, and centrifuging (4° C., 12000 rpm) for 15 min; adding an equal volume of isopropanol into the supernatant and leaving for precipitation at room temperature for 30 min; after centrifuging (4° C., 12000 rpm) for 10 min, discarding the supernatant, washing the precipitate with 75% ethanol and then dissolving in 100 µL of DEPC treated double-distilled water. Purifying the crude RNA with $RQ_1$ RNase-Free DNase (M6101, Promega): adding $RQ_1$ reaction solution (100 mM Tris-HCl, 25 mM $MgSO_4$ and 2.5 mM $CaCl_2$, DNAase 10 U) in RNA; after being placed in a 37° C. bath for 30 min, extracting with equal volume of phenol/chloroform; adding two times volume of anhydrous ethanol into the supernatant for precipitation; after centrifuging (4° C., 12000 rpm) for 10 min, discarding the supernatant, washing the precipitate with 75% ethanol and then dissolving in 40 µL of DEPC treated double-distilled water, thereby obtaining the total RNA.

The total reaction system for cDNA synthesis is 20 µL (containing 2 µg of the total RNA, 50 mmol/L of Tris-HCl (pH 8.3), 75 mmol/L of KCl, 3 mmol/L of $MgCl_2$, 10 mmol/L of DTT, 50 µmol/L of dNTPs, 50 µmol of the anchor primer T15: TTTTTTTTTTTTTTT (SEQ ID NO: 5) (TAKARA, D510), 20 U of an RNase Inhibitor (TAKARA, D2313A), 200 U of the M-MLV reverse transcriptase (Promega, M1701)). cDNA was obtained after incubating at 37° C. for 2 hours. 1 µL of cDNA was used in a PCR reaction with the PCR primers: L: ATGCAGAGGGAGGTGGGC (SEQ ID NO: 12); R: TTATATTGTACCGTAATCCAGC (SEQ ID NO: 13).

Figure 8:
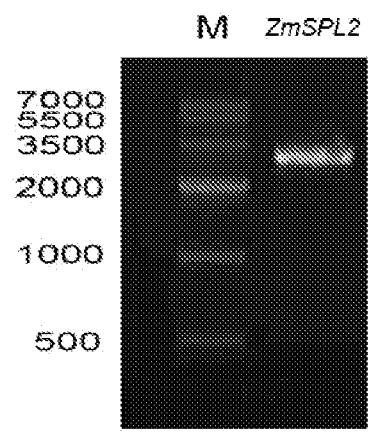
FIG. 8 shows a full length CDS amplification product of the ZmSPL2 gene.

According to the PCR results shown in FIG. 8, a single PCR product by amplification with a specific 3000 bp band was obtained. By sequencing, the gene for encoding the resultant PCR product has the nucleotide sequence as set forth in SEQ ID NO: 3 with a coding region of nucleotides of positions 1-3339 from 5' end to 3' end. This gene is designated as ZmSPL2, and the protein coded by the gene is designated as ZmSPL2 which has the amino acid sequence as set forth in SEQ ID NO: 4.

Sequencing for the specific band (SEQ ID NO: 3) and determining its chromosomal localization, it was found that it is within the 4.08 Bin region on chromosome 4. Next, an analysis on the amino acid sequence of the ZmSPL2-encoded protein was performed, and the result is that a SBP-box domain is present at N-terminal of this sequence. In addition, a homology evaluation analysis was performed on corn and *Arabidopsis thaliana* SPL proteins with the N-J method in MEGA4.1 software.

Figure 9:
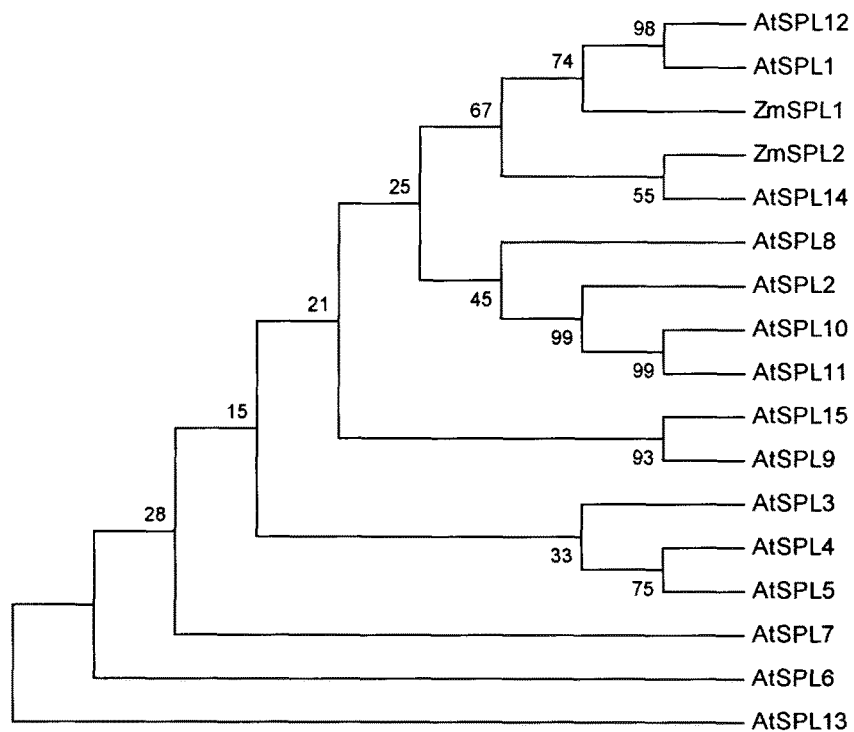
FIG. 9 shows the clustering analysis result of ZmSPL2 and *Arabidopsis thaliana* AtSPL.

The results are shown in FIG. 9, showing that ZmSPL2 is highly similar with a class of SPL coding the longest amino acid sequence (AtSPL4, AtSPL16) in *Arabidopsis thaliana*.

3. Measurement of ZmSPL2 Gene Expression in Different Plant Sites by Real-Time Fluorescence Quantitative PCR The real-time fluorescence quantitative PCR assay was performed on a Bio-Rad C1000 cycler real-time PCR system, and the reaction system of 10 µL contains 1 µL of cDNA, 0.2 µM of real-time quantitative primers and 5 µL of SYBR Premix Ex Taq (DRR041D). The real-time quantitative primers have the following sequences: SPL2-L: CTGCTCTGGCCCTATTTCTG (SEQ ID NO: 8) SPL2-R: GCATCGCTCCTCAAGGTCT (SEQ ID NO: 9). The cDNAs from 11 tissues or organs of corn inbred line Zong31 in different developmental stages were used as templates, i.e. a root and a leaf from a plant of seeding stage (day 8); a stem, an internode, a bracteal leaf, a flower filament, an immature corn ear and tassel from a plant of 60-day growth, and a seed coat, an embryo and an endosperm from a plant 15 days after pollination. The PCR protocol are as follows: denaturation at 94° C. for 5 min; then denaturation at 94° C. for 10 s, annealling at 60° C. for 20 s, and extension at 72° C. for 30 s, 35 cycles; final extension at 72° C. for 7 min. The melting curve was plotted at 65° C.-98° C. Then, a quantitative analysis was performed on the real-time quantitative PCR results using a comparison threshold method with a manually set fluorescence threshold, determining a specific cycle number, Ct value, under such a threshold and calculating the C value for each tissue or organ based on the Ct value, wherein $C=2^{-\Delta Ct}$, and $\Delta Ct=Ct_{target\ gene}-$ $Ct_{internal\ standard}$. A significance test was performed with the two-tail equal variance t test (p<0.05). This experiment include 3 biological repeats.

corn 18S rRNA gene was used as a control, the primer sequences are L: ACATGCGCCTAAGGAGAAATAG (SEQ ID NO: 10); R: ACCTCCATGCTCACTGGTACTT (SEQ ID NO: 11).

Figure 10:
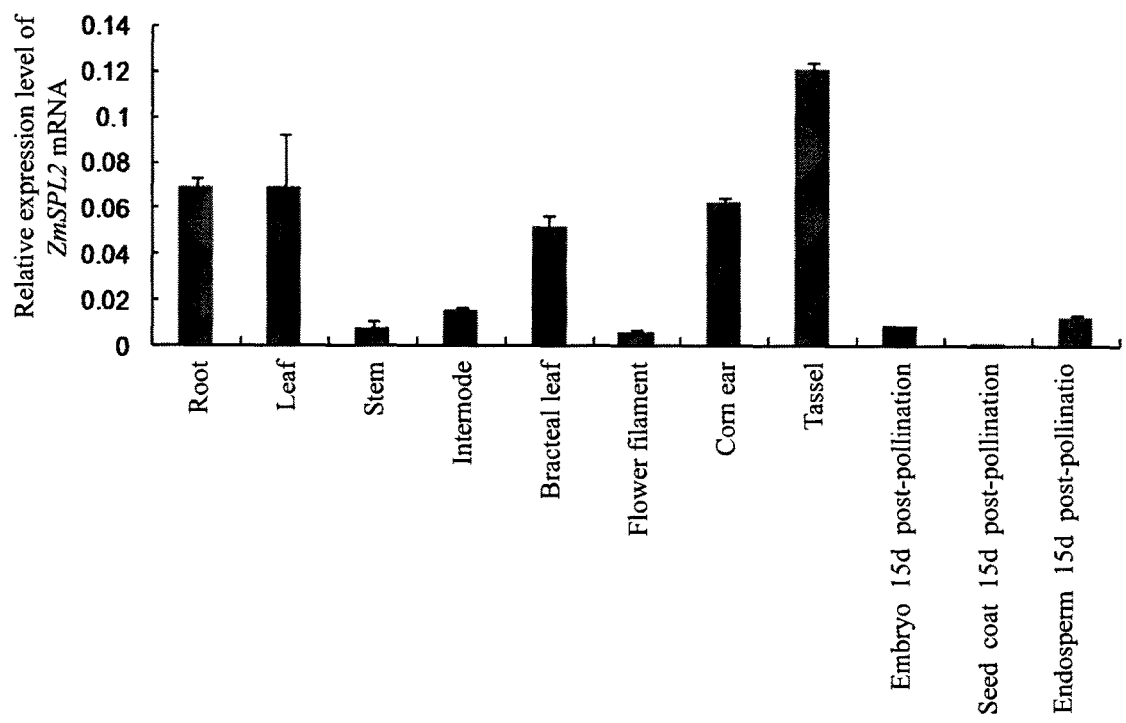
FIG. 10 shows the expression of ZmSPL2 in different corn tissues.

According to the results shown in FIG. 10, ZmSPL2 shows significant variations in the expression level between different tissues or organs. The ZmSPL2 gene has the highest expression level in the immature corn ear and tassel, and has a very low expression level in the developing embryo, endosperm, seed coat, root and flower filament.

Example 4. Use of the ZmSPL2 Gene

Through the Gateway technique, an overexpression vector of the corn ZmSPL2 gene was constructed. The *E. coli* strain is DH5α and the *Agrobacterium* strain is GV3101.

1. Construction of the Overexpression Vector

Through the Gateway technique, the vector was constructed according to the following procedure: incorporating a gateway BP reaction linker to 5' end of a primer, obtaining the target gene fragments having the linker sequence by PCR amplification, recovering the products via a agarose gel, mixing the recovered products with the vector pDONR221 in a certain ratio, and under the catalysis of BP Clonase™ enzyme, substituting the target gene into the pDONR221 vector. The constructed vector is an entry vector. Then, the inventors operated as follows: mixing the constructed entry vector containing the target gene with a destination vector in a certain ratio, and under the catalysis of the LR Clonase™ enzyme, substituting the target gene contained in the entry vector into the destination vector, thereby obtaining the overexpression vector containing the target gene.

(1) BP Reaction
BP Reaction System:

| | |
|---|---|
| The BP plasmid obtained from the above step (1) (100 fmol) | 3.5 ul |
| The destination vector pB2GW7 (Invitrogen, 11791019, 150 ng/ul) | 0.5 ul |
| LR Clonase ™ enzyme mixture | 1.0 ul |
| To a total volume | 5.0 ul |

Warming the reaction in a bath of 25° C. for 16 h.
Screening and Identification of BP Reaction Target Gene Clones a. transforming competent cells of *E. coli* DH5α with 2 ul of the BP reaction products, and culturing invertedly at 37° C. for 16 h (in a kan resistive culture medium);

b. picking up a single clone, and culturing at 37° C. with shaking at 200 rpm (adding 50 ug/ml Kan);

c. extracting plasmids, and amplifying with the gene specific primers L: ATGCAGAGGGAGGTGGGC (SEQ ID NO: 12) and R: TTATATTGTACCGTAATCCAGC (SEQ ID NO: 13) to obtain an amplification product;

d. sequencing for the amplification product and comparing with the original sequence. The plasmid whose amplification product has the sequence of SEQ ID NO: 3 is the entry vector BP plasmid.

(2) LR Reaction
Performing an LR reaction using the obtained entry vector of the corn ZmSPL2 gene with a reaction system as below:

| | |
|---|---|
| The PCR product obtained form step 2 of example 3 (100 fmol) | 3.5 ul |
| pDONR ™ vector (Invitrogen, 12536-017, 150 ng/ul) | 0.5 ul |
| BP Clonase ™ enzyme mixture (Invitrogen, 11789-013) | 1.0 ul |
| To a total volume | 5.0 ul |

Warming in a bath of 25° C. for 16 h.
Screening and Identification of LR Reaction Target Gene Clones (1) transforming competent cells of *E. coli* DH5α with 2 ul of the LR reaction products, and culturing invertedly at 37° C. for 12-16 h (in a spectinomycin resistive culture medium);

(2) picking up a single clone, and culturing at 37° C. with shaking at 180-200 rpm (adding 50 ug/ml spectinomycin);

(3) extracting plasmids, and amplifying with the gene specific primers L: ATGCAGAGGGAGGTGGGC (SEQ ID NO: 12) and R: TTATATTGTACCGTAATCCAGC (SEQ ID NO: 13) to obtain an amplification product.

The amplification product was sequenced. The plasmid having the sequence of SEQ ID NO: 3 is the overexpression vector which is obtained by inserting the sequence of SEQ ID NO: 3 into the pB2GW7 plasmid with the Gateway™ technique. This plasmid is designated as pB2GW7-ZmSPL2.

2. Preparation of the ZmSPL2 Transgenic *Arabidopsis thaliana*

(1) Preparation of *Agrobacterium* Competent Cells a. Picking up a single colony of *Agrobacterium tumefaciens* GV3101 (Ectopic overexpression of wheat TaSrg6 gene confers water stress tolerance in *Arabidopsis*. Tong S M, Ni Z F, Peng H R, Dong G Q, Sun Q X. 2007, 172(6): 1079-1086, available publically from the China Agricultural University) in 3 ml of YEB liquid medium (containing a corresponding antibiotic, 100 μg/ml Rif), and culturing with shaking at 28° C. overnight;

b. Inoculating 500 μl of the overnight cultured bacterial liquid in 50 ml YEB liquid medium (containing a corresponding antibiotic), and culturing at 28° C. with shaking until reaching $OD_{600}$ of 0.5;

c. centrifuging at 5000 rpm for 5 min;

d. adding 10 ml of 0.15 mmol/L NaCl to suspend the *agrobacterium* cells, and centrifuging at 5000 rpm for 5 min;

e. suspending the cells in 1 ml of precooled 20 mmol/L $CaCl_2$, and storing in an ice bath until use within 24 h, or subdividing into 200 μl/tube; quick freezing in liquid nitrogen for 1 min, and storing under −80° C. until use.

(2) Preparation and Identification of Positive *Agrobacterium* Clones a. slowly thawing 200 μl of competent cells on ice for 30 min;

b. adding 1 μg of the constructed plasmid pB2GW7-ZmSPL2, and placing on ice for 30 min;

c. quick freezing in liquid nitrogen for 2 min, placing in a water bath of 37° C. for 5 min and on ice for 2 min;

d. then adding into 1 ml YEB culture medium, and culturing at 28° C. with shaking slowly for 4 h;

e. centrifugating at 4000 rpm for 5 min, and discarding the supernatant 900 μl;

f. spreading the remaining liquid on a YEB plate containing 50 μg/ml of spectinomycin and 100 μg/ml of Rif, and culturing at 28° C. for 2 days;

g. picking up a single colony grown on the plate, inoculating in a YEB liquid medium (containing 50 μg/ml of spectinomycin and 100 μg/ml of Rif) in a ratio of 1:50, and culturing at 28° C. with shaking overnight.

Extracting the plasmid from recombinant bacteria and amplifying with the gene specific primers L: ATGCAGAGGGAGGTGGGC (SEQ ID NO: 12) and R: TTATATTGTACCGTAATCCAGC (SEQ ID NO: 13) to obtain a 3000 bp product, which represents positive recombinant bacteria designated as GV3101/pB2GW7-ZmSPL2.

(3) Transformation of *Arabidopsis thaliana* a. vernalizing the seeds of Columbia wild type *Arabidopsis thaliana* (col-0, Yao Y, Ni Z, Du J, Han Z, Chen Y, Zhang Q, Sun Q. Ectopic overexpression of wheat adenosine diphosphate-ribosylation factor, TaARF, increases growth rate in *Arabidopsis*. J Integr Plant Biol. 2009, 51(1):35-44, available publically from the China Agricultural University) (hereinafter referred to as wild-type *Arabidopsis thaliana*) at 4° C. for 72 h, sowing in a MS culture medium and cultivating at 20° C. in a cultivation chamber of 60% humidity at a 16 h light/8 h dark photoperiod; after growing with two true leaves, transplanting the seedlings in a planting bowl containing a mixture of a nutrient soil and vermiculite in an equal ratio.

b. after flowering, cutting the tip of bough to facilitate the development of lateral branchs. Within 6 days after pruning, preparing the plant for *agrobacterium* transformation;

c. inoculating the *agrobacterium* GV3101/pB2GW7-ZmSPL2 in a culture medium containing 5 ml YEB+100 μg/ml SP+100 μg/ml Rifampin, culturing with shaking for overnight, and transferring to 500 ml YEB liquid medium the next day for culturing at 28° C. until to $OD_{600}$ of about 0.8;

d. collecting thallus by configuration, and suspending the *agrobacterium* bacteria in a transformation buffer. 4 days after pruning, dipping the plants in the transformation buffer invertedly;

e. taking the planting plate and encasing with a black plastic bag filled with air, placing horizontally; after cultivating at 20° C. in dark for 24 h, removing the plastic bag and standing the planting bowl upright. Cultivating the plants under normal light and temperature conditions until seeding. Harvesting the mature $T_0$ seeds of the ZmSPL2 transgenic *Arabidopsis thaliana*.

(4) Screening Positive Seedlings of Transgenic *Arabidopsis thaliana*

Preparing an MS plate, sterilizing the $T_0$ seeds of ZmSPL2 transgenic *Arabidopsis thaliana* prior to washing 6 times with sterile water; spreading the seeds on a selective MS culture medium (125 μL/L Basta), after vernalizing at 4° C. for 3 days, transferring to a green house at 20° C. and a 16 h light/8 h dark photoperiod and selecting the positive plants after 7-day cultivation. The positive plants have the following characteristics: healthy true leaf in dark green color and roots stretching into the culture medium.

Extracting genomic DNA from the positive plants obtained through the above primary screen, amplifying with the gene specific primers L: ATGCAGAGGGAGGTGGGC (SEQ ID NO: 12) and R: TTATATTGTACCGTAATCCAGC (SEQ ID NO: 13) to obtain a 3000 bp product, which indicates that it is a positive $T_0$ plant of ZmSPL2 transgenic *Arabidopsis thaliana*. In total 100 positive $T_0$ plants of ZmSPL2 transgenic *Arabidopsis thaliana* were obtained.

Transferring the above positive $T_0$ plants of ZmSPL2 transgenic *Arabidopsis thaliana* to a normal culture medium, transplanting into soil after 10 days, and harvesting $T_1$ seeds after 50-day growth. Cultivating and screening the $T_1$ seeds in a same method, transplanting and harvesting $T_2$ seeds in a segregation ratio of 3:1 from individual plants. Cultivating 10 plants for each $T_2$ plant line and screening in a same manner to obtain pure line without segregation, thereby obtaining the ZmSPL2 transgenic *Arabidopsis thaliana* $T_2$ plants.

Using the same procedure, transforming the empty vector pB2GW7 into the wild-type *Arabidopsis thaliana* to obtain empty vector transformed *Arabidopsis thaliana* $T_0$ plants. Extracting RNA, preparing cDNA through reverse transcription, and amplifying with the gene specific primers L: ATGCAGAGGGAGGTGGGC (SEQ ID NO: 12) and R: TTATATTGTACCGTAATCCAGC (SEQ ID NO: 13). No target fragment was obtained, which indicates that it is a positive empty vector transformed *Arabidopsis thaliana*. Similarly, after harvesting and sowing, the empty vector transformed *Arabidopsis thaliana* $T_2$ plants were finally obtained.

3. Phenotypic Studies of the ZmSPL2 Transgenic *Arabidopsis thaliana*

1) Seed Study (1) Microscopic Observations on the Morphology of *Arabidopsis thaliana* Seeds after Pollination a. placing the $T_2$ seeds of ZmSPL2 transgenic *Arabidopsis thaliana* (ZmSPL2-OX) 7 days after pollination in a 50% FAA fixation liquid until use.

b. removing the seeds from the FAA fixation liquid and pacing serially in 70%, 85% and 95% ethanol each for 30 min, then transferring into 100% ethanol for dehydration 3 times, each for 1 h, and overnight for the last time.

c. next day, placing the seeds in a mixture of 100% ethanol and wintergreen oil (1:1) for 1 h, then transferring into wintergreen oil for clarifying 3 times, each for 1 h, and over 1 day for the last time.

d. toluidine blue staining: staining in a toluidine blue working liquid for 3 minutes, color separating in 95% alcohol for 1 minute, two times, dehydrating in 100% alcohol and clarifying in wintergreen oil.

e. finally, mounting with Canadian resin, and after drying, observing the shape and contour of lodicule as well as the central cell structure on a Nikon Ti differential interference contrast microscope and taking pictures.

Wild-type *Arabidopsis thaliana* (WT) and empty vector transformed *Arabidopsis thaliana* $T_2$ plant are used as controls, and 30 seeds for each plant line were evaluated, and the experiment were repeated three times and a mean was taken for the results.

Figure 11:
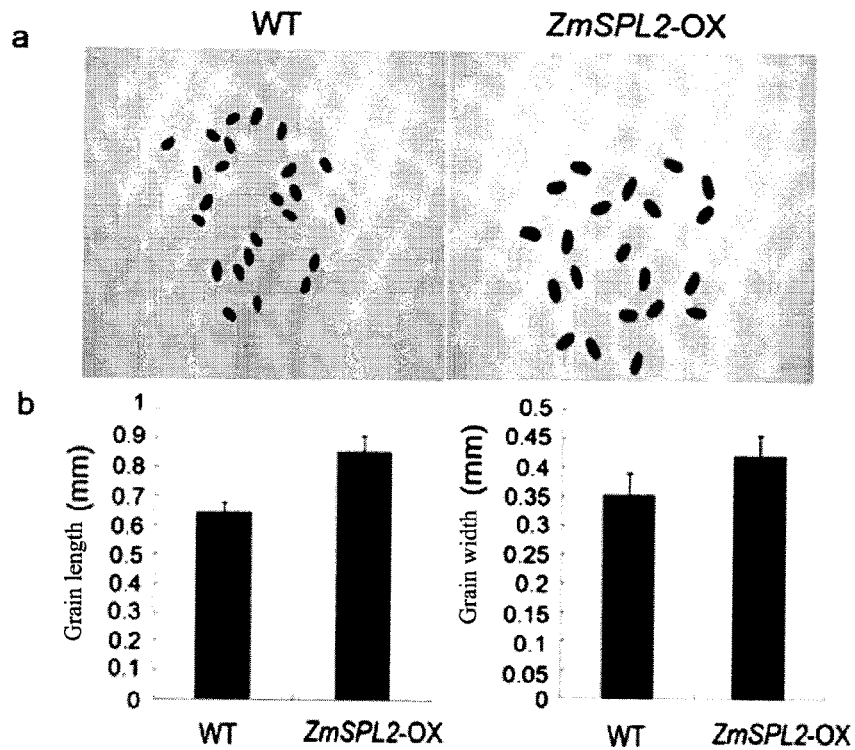
FIG. 11 shows the phenotypic characteristics of seeds in a ZmSPL2-overexpressed transgenic *Arabidopsis thaliana*.

The results are shown in FIG. 11a. It can be seen that, compared to the wild-type *Arabidopsis thaliana* seeds, the $T_2$ seeds of ZmSPL2 transgenic *Arabidopsis thaliana* (ZmSPL2-OX) are bigger. This mainly manifests in the grain length (under a magnification of 11.5 of the microscope).

Quantifying the grain length and grain width statistically. According to the results shown in FIG. 11b, the $T_2$ seeds of ZmSPL2 trans genic *Arabidopsis thaliana* (ZmSPL2-OX) and the wild-type *Arabidopsis thaliana* seeds (WT) have a grain length of 0.86 and 0.645 mm respectively, and a grain width of 0.4211 and 0.352 (mm) respectively.

There is no significant difference between the wild-type *Arabidopsis thaliana* (WT) and the empty vector transformed *Arabidopsis thaliana* $T_2$ plant.

(2) Seed Development and Seed Weight

A mature *Arabidopsis thaliana* seed has been found mainly consisting of an embryo, and the endosperm gradually degrades to disappear as the seed develops. Thus, further dynamically observing the embryos of seeds 5-9 days after pollination from the ZmSPL2 transgenic *Arabidopsis thaliana* $T_2$ plant (ZmSPL2-OX), the empty vector transformed *Arabidopsis thaliana* $T_2$ plant and the wild-type

*Arabidopsis thaliana* plant (WT) by TBO staining (with the same procedure in above step (1)).

Figure 12:
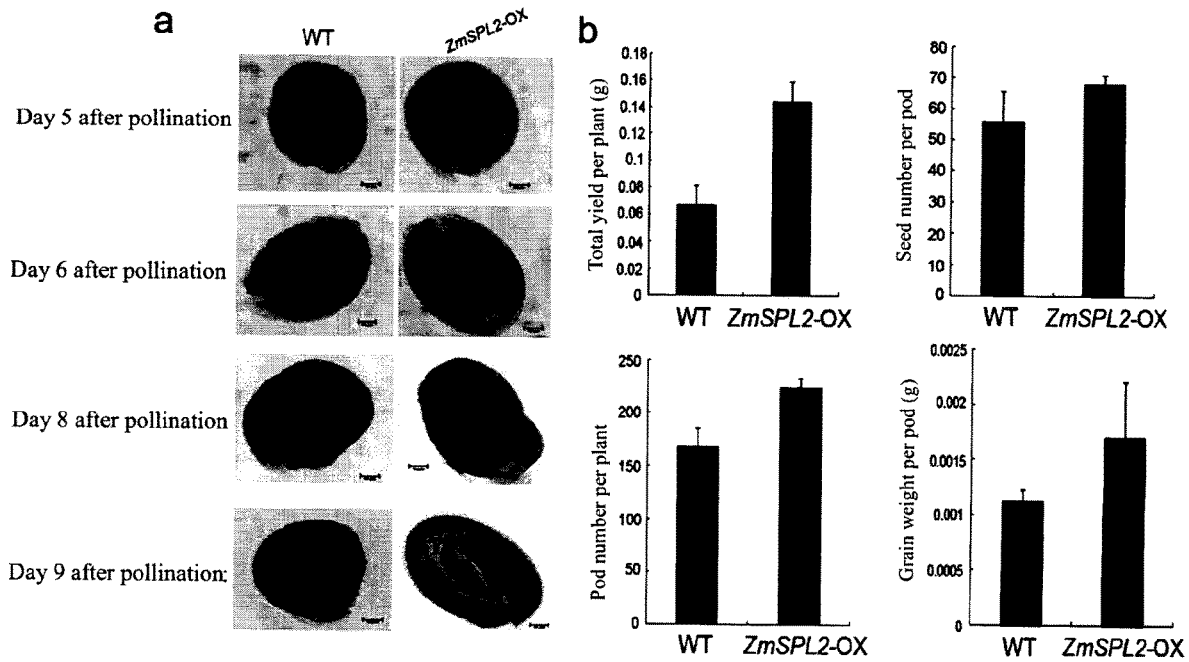
FIG. 12 shows the phenotypic characteristics of seeds and embryos after pollination in a ZmSPL2-overexpressed transgenic *Arabidopsis thaliana* and a wild-type plant.

The morphological observations of the embryos after pollination are shown in FIG. 12a. On day 5 after pollination, when the wild-type seeds are in the early heart stage, the transgenic seeds are still in the globular stage; and on day 9 after pollination, the wild-type seeds almost fill fully inside the seed coat, but the embryos in the transgenic seeds have much space for development. These results demonstrate that, with the overexpression of ZmSPL2 gene, the development of *Arabidopsis thaliana* seeds shows retardation, therefore there is a greater storage capacity in the seed.

FIG. 12b shows the statistic results of yields, 3 plants for each plant line, and repeating the experiment 3 times. The results were averaged out.

According to the results, it can be seen:

For the ZmSPL2 transgenic *Arabidopsis thaliana* $T_2$ plant (ZmSPL2-OX) and the wild-type *Arabidopsis thaliana* plant (WT), the total yield per plant is 0.1443 and 0.0669 g respectively;

For the ZmSPL2 transgenic *Arabidopsis thaliana* $T_2$ plant (ZmSPL2-OX) and the wild-type *Arabidopsis thaliana* plant (WT), the number of seeds per pod is 68 and 55.5 respectively;

For the ZmSPL2 transgenic *Arabidopsis thaliana* $T_2$ plant (ZmSPL2-OX) and the wild-type *Arabidopsis thaliana* plant (WT), the pods number per plant is 225 and 167.3 respectively;

For the ZmSPL2 transgenic *Arabidopsis thaliana* $T_2$ plant (ZmSPL2-OX) and the wild-type *Arabidopsis thaliana* plant (WT), the grain weight per pod is 0.0017 and 0.001125 g respectively.

There is no significant difference between the wild-type *Arabidopsis thaliana* plant (WT) and the empty vector transformed *Arabidopsis thaliana* $T_2$ plant.

So, it can be seen that overexpression of ZmSPL2 may increase the weight.

2) Development of Root System

A germination test (at 20° C. temperature and a 16 h light/8 h dark photoperiod) was performed on seeds from two plant lines ZmSPL2-OX-1 and ZmSPL2-OX-2 of the ZmSPL2 transgenic *Arabidopsis thaliana* $T_2$ plant (ZmSPL2-OX), the empty vector transformed *Arabidopsis thaliana* $T_2$ plant and the wild-type *Arabidopsis thaliana* plant (WT).

Figure 13:
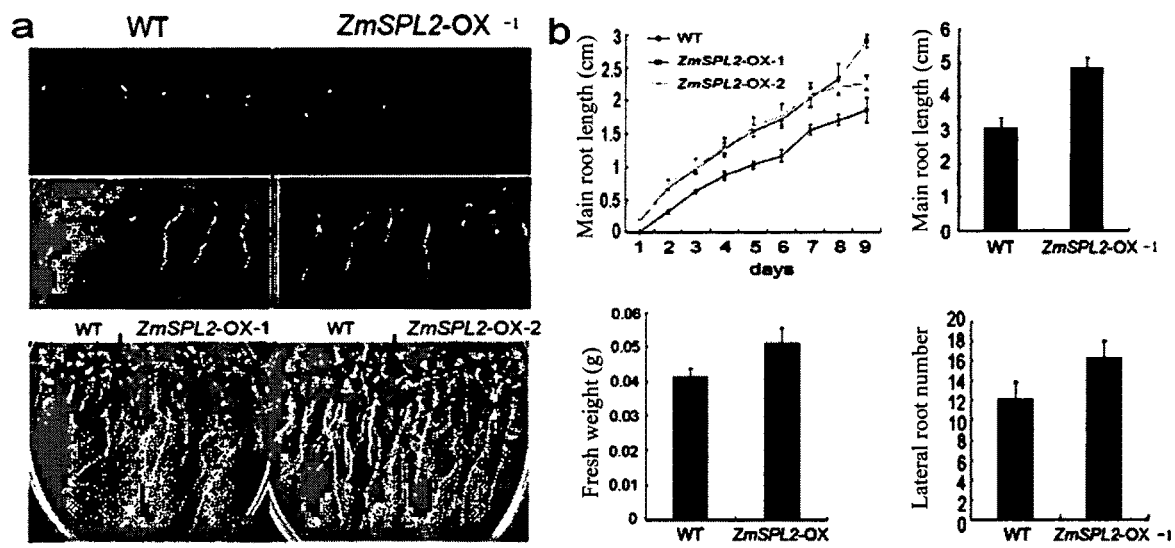
FIG. 13 shows the phenotypic characteristics of root system in a ZmSPL2-overexpressed transgenic *Arabidopsis thaliana*.

The phenotypic results are shown in FIG. 13a, in which the three rows in the figure represent the results obtained on day 2, 7 and 14 after sowing. It can be seen that the ZmSPL2-OX-1 and ZmSPL2-OX-2 seeds germinate faster than the wild-type *Arabidopsis thaliana* seeds and have a higher growth rate of the whole root system than the wild-type *Arabidopsis thaliana*.

Quantifying the main root length, the number of lateral roots and root fresh weight statistically. 3 plants for each plant line, and repeating the experiment 3 times. The results were averaged out.

The results are shown in FIG. 13b (the main root length on day 14 is not shown).

On day 1-9, ZmSPL2-OX-1 has a main root length of 0.176667, 0.727917, 1.005208, 1.28125, 1.597917, 1.77125, 2.095833, 2.2125 and 2.266667 cm respectively;

On day 1-9, ZmSPL2-OX-2 has a main root length of 0.19, 0.716667, 1.125, 1.3125, 1.625, 1.85, 2.06667, 2.23333 and 2.4 cm respectively;

On day 1-9, WT has a main root length of 0, 0.305, 0.620833, 0.866667, 1.016667, 1.155556, 1.544, 1.7 and 1.85 cm respectively;

On day 14, ZmSPL2-OX-1 and WT has a main root length of 4.88 and 3.09 cm respectively;

On day 14, ZmSPL2-OX-1 and WT has a total root fresh weight of 0.051 and 0.0415 g respectively;

On day 14, ZmSPL2-OX-1 and WT has a lateral root number of 16.4 and 12.17 respectively.

There is no significant difference between the wild-type *Arabidopsis thaliana* plant (WT) and the empty vector transformed *Arabidopsis thaliana* $T_2$ plant.

So, it can be seen that overexpression of ZmSPL2 increase the main root length, the lateral root number and the root fresh weight.

3) Leaf

The $T_2$ seeds of ZmSPL2 transgenic *Arabidopsis thaliana* (ZmSPL2-OX), the $T_2$ seeds of empty vector transformed *Arabidopsis thaliana* and the wild-type *Arabidopsis thaliana* seeds (WT) (at a temperature of 20° C. and a 16 h light/8 h dark photoperiod) were sowed.

Meanwhile, observing the leaf cells microscopically on day 25 according to the following specific procedure:

a) boiling fresh leaves of *Arabidopsis thaliana* in water to kill cells, then pouring out the water with dissolved pigments;

b) transferring the material into 95% ethanol, and boiling until the tissue discolor completely (about 1 hour);

c) placing the still warm, discolored material into 85% lactic acid preheated to 96° C., and obtaining transparent tissue material after 8 minutes;

d) transferring the transparent material in 85% lactic acid at room temperature and storing until used for mounting;

e) mounting and observing: taking the *Arabidopsis thaliana* leaves treated for transparency and sucking excess lactic acid with an absorbent paper, then mounting with ethylene glycol and observing under a microscope.

Figure 14:
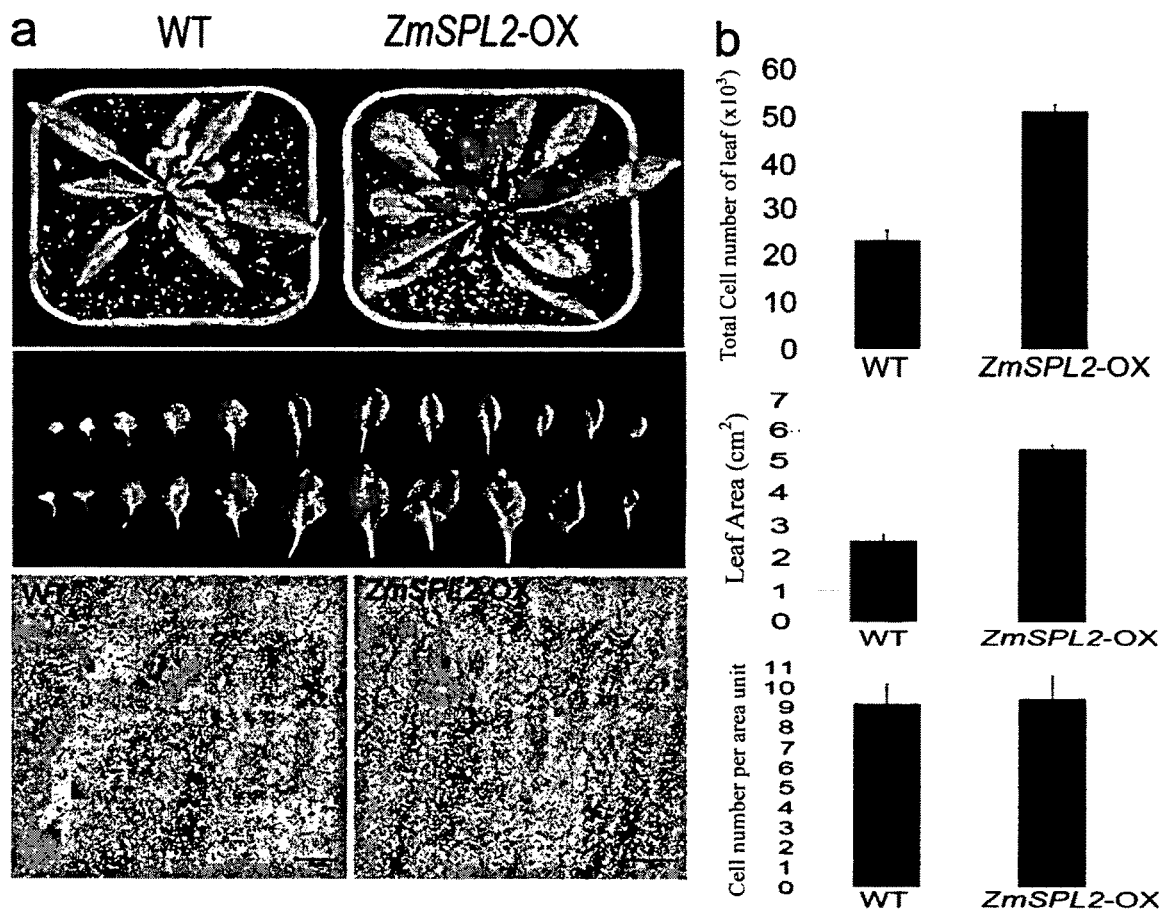
FIG. 14 shows the phenotypic characteristics of leafs in a ZmSPL2-overexpressed transgenic *Arabidopsis thaliana* and a wild-type plant.

On day 25, investigating the phenotypes of above-ground plant parts. The results are shown in FIG. 14a, wherein the first, second and third row represent the above-ground parts, rosette leaf and leaf cells of the wild-type and ZmSPL2 transgenic *Arabidopsis thaliana* on day 25. It can be seen that the above-ground parts of the ZmSPL2 overexpressed plant are larger than those of the wild-type plants.

Quantifying the leaf area, leaf number and leaf cell number of rosette leaf on day 25 statistically. The measurement of leaf area may be carried out through any conventional method known in the art, such as the grid-point method, graph paper method, and paper weighing method, or leaf area may be measured with a leaf area meter such as LAI-3100 area meter from LI-COR. Some leaf area prediction models are also useful in measurement of leaf area (see, e.g., Sezer I, Oner F, Mut Z., Non-destructive leaf area measurement in maize (*Zea mays* L.), J Environ Biol. 2009 September; 30 (5 Suppl): 785-90). The leaf number may be determined by direct counting or may be estimated according to single-side leaf vein number. The leaf cell number may be measured by the flow cytometry which is well-known in the art. 3 plants are measured for each plant line, and the experiment is repeated for 3 times. The results are averaged out.

The results are shown in FIG. 14b.

For the ZmSPL2 transgenic *Arabidopsis thaliana* $T_2$ plant (ZmSPL2-OX) and the wild-type *Arabidopsis thaliana* plant (WT), the leaf area of rosette leaf is 5.427 and 2.558 $cm^2$ respectively;

For the ZmSPL2 transgenic *Arabidopsis thaliana* $T_2$ plant (ZmSPL2-OX) and the wild-type *Arabidopsis thaliana* plant (WT), the cell number per area unit of rosette leaf is 9.48 and 9.23 respectively;

For the ZmSPL2 transgenic *Arabidopsis thaliana* T$_2$ plant (ZmSPL2-OX) and the wild-type *Arabidopsis thaliana* plant (WT), the leaf cell number of rosette leaf is 51.45×10$^3$ and 23.61×10$^3$ respectively.

There is no significant difference between the wild-type *Arabidopsis thaliana* plant (WT) and the empty vector transformed *Arabidopsis thaliana* T$_2$ plant.

Through further investigation, the enlargement of above ground parts is found mainly present as increase of the rosette leaf area. From the microscopic observation of leaf epidermal cells, it is indicated that the leaf is enlarged mainly as a result of the increased cell number instead of the increased cell volume.

Example 5. Identification of the Biological Functions of ZmSPL1 and ZmSPL2 Overexpressed Rice In order to investigate the biological functions of the ZmSPL genes, the overexpression vectors of ZmSPL1 and ZmSPL2 genes were constructed, and the rice Kitaake was transformed via *agrobacterium* transformation to obtain 14 ZmSPL1 overexpressed plants and 10 ZmSPL2 overexpressed plants.

Firstly, the grain size of the transgenic and control rice was analyzed. The results show that, comparing with control, ZmSPL1 and ZmSPL2 overexpressed plants have bigger grains. According to the statistic results of grain length and grain width, the transgenic rice has a greater grain length, but the grain width does not change significantly. Specifically, the transgenic plant lines ZmSPL1-OX-1, ZmSPL1-OX-5, ZmSPL1-OX-18, ZmSPL2-OX-8 and ZmSPL2-OX-12 have significantly increased grain sizes than the control, having the average grain lengths of 7.71 mm, 7.36 mm, 7.75 mm, 7.72 mm and 7.47 mm respectively, and when comparing with the average grain length of 7.21 mm for the control, increasing by 6.93%, 2.08%, 7.49%, 7.07% and 3.61% respectively (see FIGS. 15 and 16).

The 1000-grain weight of the transgenic and control rice were also analyzed. The results indicate that most of ZmSPL1 and ZmSPL2 overexpressed plants have an increased 1000-grain weight, wherein the significantly increased plant lines ZmSPL1-OX-6, ZmSPL1-OX-15, ZmSPL1-OX-1, ZmSPL2-OX-6, ZmSPL2-OX-8 and ZmSPL2-OX-7 haves a 1000-grain weight of 27.42±1.10 g, 26.16±1.50 g, 26.00±3.30 g, 27.67±1.28 g, 25.32±1.00 g and 25.09±2.19 g respectively, increasing by 21.49%, 15.91%, 15.20%, 22.60%, 12.18% and 11.17% respectively in comparison with the control (having a 1000-grain weight of 22.57±1.02 g) (see FIG. 17).

Example 6. Identification of the Biological Functions of ZmSPL1 Overexpressed Corn In order to investigate the biological functions of the ZmSPL1 gene, an overexpression vector of ZmSPL1 gene was constructed, and the corn inbred line Zhen58 was transformed through the infection of corn shoots with *agrobacterium* LBA4404 to obtain the transgenic plants and identify 26 positive plant lines through PCR. FIG. 18 shows the PCR identification of some positive plants.

When compared with Zhen58, most ZmSPL1 overexpressed plants were found to have an increased 100-grain weight. The statistic results indicate that the significantly increased plant lines ZmSPL1-OX-2, ZmSPL1-OX-21, ZmSPL1-OX-25, ZmSPL1-OX-1 and ZmSPL1-OX-15 have a 100-grain weight of 24.6±1.67 g, 24.0±1.86 g, 24.0±2.09 g, 23.8±1.25 g and 23.5±0.14 g respectively, increasing by 22.39%, 19.40%, 19.40%, 18.41% and 16.92% respectively in comparison with the control Zhen58 (having a 100-grain weight of 20.1±1.87 g) (see FIG. 19). This suggests that ZmSPL1 can increase the grain size and weight of corn.

Example 7. Results of a Plot Experiment of ZmSPL1-OX Corn

In order to further investigate the biological functions of the ZmSPL1 gene, we conduct a plot experiment of ZmSPL1 overexpressed corn. 10 transgenic T3 lines with evident phenotype and the control Zhen58 are used in the experiment, i.e. ZmSPL1-OX-2-10, ZmSPL1-OX-10-1, ZmSPL1-OX-21-10, ZmSPL1-OX-26-6, ZmSPL1-OX-21-11, ZmSPL1-OX-25-3, ZmSPL1-OX-1-6, ZmSPL1-OX-15-8, ZmSPL1-OX-16-7, ZmSPL1-OX-22-3 and Zhen58. All of them are grown in the Shangzhuang experiment station, Beijing, each line in one plot with 5 rows, 15 plants in one row. The natural pollination is used. And the spike and grain traits are studied for the progenies.

In terms of the spike traits, the present study finds that, in comparison with the control Zhen58, the ZmSPL1 overexpressed corn lines exhibit increased spike length and spike width (FIGS. 20 and 21), wherein Zhen58 has a spike length of 16.35±0.95 cm, while the line ZmSPL1-OX-25-3 shows a more different spike length of 18.04±0.50 cm, increasing by 10.34% than the control (FIG. 22); and Zhen58 has a spike width of 4.03±0.14 cm, while the line ZmSPL1-OX-25-3 shows a more different spike width of 4.62±0.27 cm, increasing by 14.64% than the control (FIG. 23). However, there is no significant difference in the grain row number and the grain number of row between the transgenic lines and the control (FIGS. 24 and 25).

In further investigation on grain size of the transgenic corn lines, we find that, in comparison with the control Zhen58, the ZmSPL1 overexpressed corn lines have greater grains and an increased 100-grain weight (FIG. 26). The control Zhen58 has a 100-grain weight of 31.30±1.94 g, while the lines ZmSPL1-OX-22-3, ZmSPL1-OX-15-8, ZmSPL1-OX-25-3, ZmSPL1-OX-1-6 and ZmSPL1-OX-21-11 have higher 100-grain weights of 34.12±2.16 g, 34.32±1.91 g, 34.42±2.13 g, 36.27±2.30 g and 36.48±2.48 g respectively, increasing by 9.01%, 9.65%, 9.97%, 15.88% and 16.49% respectively than the control (FIG. 27).

Example 8. Results of a Plot Experiment of ZmSPL1-OX Rice

We also conduct a plot experiment of ZmSPL overexpressed rice. 6 ZmSPL1 T2 lines and 4 ZmSPL2 T2 lines with evident phenotype and the control Kitaake are used in the experiment, i.e. ZmSPL1-OX-1, ZmSPL1-OX-5, ZmSPL1-OX-6, ZmSPL1-OX-15, ZmSPL1-OX-17, ZmSPL1-OX-18, ZmSPL2-OX-6, ZmSPL2-OX-7, ZmSPL2-OX-8, ZmSPL2-OX-11 and the control. All of them are grown in the Shangzhuang experiment station, Beijing, each line in one plot with 2 rows, 11 plants in one row. The progenies are investigated for their grain traits.

Comparing with the control, the transgenic lines have an increased grain length, but the grain width change is insignificant (FIGS. 28 and 29). The control has an average grain length of 0.67±0.04 cm, while ZmSPL1-OX and ZmSPL2-OX have an average grain length of 0.71±0.04 cm and 0.72±0.04 cm respectively, increasing by 5.97% and 7.46% than the control (FIGS. 30 and 31).

Comparing the grain size of each transgenic line with the control, the results show that the transgenic lines ZmSPL1-OX-17, ZmSPL1-OX-18, ZmSPL2-OX-7 and ZmSPL2-OX-11 have greater grain sizes, and their grain length are 0.73±0.06 cm, 0.73±0.04 cm, 0.73±0.04 cm and 0.73±0.03 cm respectively, all increasing by 13.43% than the control (FIGS. 32 and 33). However, their grain widths are not significantly different from the control (FIGS. 32 and 34).

After removal of the grain husk, we compare the size of inside grains and the results show that ZmSPL1-OX and ZmSPL2-OX both have increased grain length than the control (FIG. 35), but insignificantly different grain width (FIGS. 36 and 38). The control has an average grain length of 0.46±0.03 cm, while ZmSPL1-OX and ZmSPL2-OX have an average grain length of 0.52±0.02 cm and 0.51±0.03 cm respectively, increasing by 13.04% and 10.87% respectively than the control (FIG. 37).

We also analyze the 1000-grain weight of the transgenic rices and the control, and the results show that the ZmSPL1 and ZmSPL2 overexpressed lines have an increased 1000-grain weight, wherein the lines ZmSPL1-OX-6, ZmSPL1-OX-1, ZmSPL1-OX-18, ZmSPL2-OX-8, ZmSPL2-OX-7 and ZmSPL2-OX-6 have a 1000-grain weight of 26.34±1.12 g, 27.29±0.68 g, 28.13±0.88 g, 26.10±0.33 g, 26.50±0.41 g and 27.85±0.34 g respectively, increasing by 10.62%, 14.62%, 18.14%, 9.62%%, 11.30% and 16.97% respectively than the control (with a 1000-grain weight of 23.81±0.17 g) (FIG. 39).

---

What is claimed is:

1. A recombinant DNA construct comprising a nucleic acid molecule comprising a promoter functional in a plant cell positioned to provide for expression of a polynucleotide having the following nucleotide sequence:
   (1) a sequence encoding the polypeptide sequence set forth in SEQ ID NO: 2 or 4; or
   (2) a sequence encoding a polypeptide having at least 99% or 99.5% sequence identity with the sequence set forth in SEQ ID NO: 2 or 4.

2. A plant cell comprising the recombinant DNA construct of claim 1.

3. A transformed plant comprising the recombinant DNA construct of claim 1.

4. A method for producing a transformed plant having an altered trait, wherein said method comprises transforming a plant with the recombinant DNA construct of claim 1 and obtaining a transformed plant that shows an altered trait selected from the group consisting of increased seed size, increased seed number, increased seed weight, increased grain size, increased grain number, increased grain weight, increased leaf size, increased leaf area, increased leaf number, increased leaf cell number, increased main root length, increased lateral root number, increased root fresh weight, and increased yield as compared to a non-transformed plant or wild-type plant.

5. A method for increasing yield of a plant, wherein said method comprises transforming a plant with the recombinant DNA construct of claim 1 and obtaining a transformed plant that shows increased yield as compared to a non-transformed plant or wild-type plant.

6. The transformed plant according to claim 3, wherein said plant has an altered trait as compared to a non-transformed plant or wild-type plant, wherein said altered trait is selected from the group consisting of increased seed size, increased seed number, increased seed weight, increased grain size, increased grain number, increased grain weight, increased leaf size, increased leaf area, increased leaf number, increased leaf cell number, increased main root length, increased lateral root number, increased root fresh weight, and increased yield.

7. The transformed plant according to claim 3, wherein said plant is a monocotyledon or dicotyledon plant.

8. The transformed plant according to claim 3, wherein said plant is selected from the group consisting of corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, strawberry, blueberry and barley.

9. The transformed plant according to claim 3, wherein said plant is *Arabidopsis thaliana*, rice or corn.

10. The recombinant DNA construct according to claim 1, wherein the polynucleotide has the following nucleotide sequence:
   (1) the sequence set forth in SEQ ID NO: 1 or 3, or the complementary sequence thereof; or
   (2) a sequence having at least 99% or 99.5% sequence identity with the sequence set forth in SEQ ID NO: 1 or 3, which encodes a protein having a function of controlling plant organ sizes.

11. The transformed plant according to claim 3, wherein said plant is a crop plant.

* * * * *